United States Patent [19]

Seto et al.

[11] Patent Number: 5,919,806
[45] Date of Patent: Jul. 6, 1999

[54] MEDICINES FOR CARDIAC INSUFFICIENCY

[75] Inventors: Kiyotomo Seto, Tokyo; Hiroo Matsumoto, Chiba-ken; Yoshimasa Kamikawaji, Chiba-ken; Kazuhiko Ohrai, Chiba-ken; Toru Yamashita; Yukinori Masuda, both of Saitama-ken, all of Japan

[73] Assignee: Nissan Chemical Industries, Ltd., Tokyo, Japan

[21] Appl. No.: 08/530,252

[22] PCT Filed: Apr. 1, 1994

[86] PCT No.: PCT/JP94/00544

§ 371 Date: Sep. 29, 1995

§ 102(e) Date: Sep. 29, 1995

[87] PCT Pub. No.: WO94/22442

PCT Pub. Date: Oct. 13, 1994

[30] Foreign Application Priority Data

Apr. 2, 1993 [JP] Japan .................................. 5-076860
Mar. 8, 1994 [JP] Japan .................................. 6-037303

[51] Int. Cl.$^6$ .................................................. A61K 31/37
[52] U.S. Cl. ........................ 514/364; 544/238; 546/197; 548/126
[58] Field of Search .......................... 514/364; 544/238; 546/197; 548/126

[56] References Cited

U.S. PATENT DOCUMENTS 4,900,752  2/1990  Seto et al. .
5,097,037  3/1992  Matsumoto et al. .
5,164,509  11/1992  Atwal ...................................... 548/128

FOREIGN PATENT DOCUMENTS 0 409 165 A2   1/1991   European Pat. Off. .
327127         8/1991   European Pat. Off. .
0 488 107 A2   6/1992   European Pat. Off. .
492391         7/1992   European Pat. Off. .
0 535 377 A2   4/1993   European Pat. Off. .
40 10 097 A 1  10/1991  Germany .
2-4791         1/1990   Japan .
2-49788        2/1990   Japan .
2-152974       6/1990   Japan .
3-141286       6/1991   Japan .
5-43432        2/1993   Japan .
5-301878       11/1993  Japan .
A-5-507645     11/1993  Japan .
WPO-91/14694   10/1991  WIPO .

OTHER PUBLICATIONS

WPIDS abstract AN 91–296642, May et al, DE 4010097, Feb. 10, 1991.
English abstract of Japanese Patent Application Laid–open No. Hei 2–4791 (1 page), (Jan. 1990).
English abstract of Japanese Patent Application Laid–open No. Hei 2–152974 (2 pages), (Jun. 1990).
English abstract of European Patent No. 492,391 (2 pages), (Jul. 1992).
English abstract of European Patent No. 327,127 (1 page), (Feb. 1988).
Longman, Susan D. et al., "Potassium Channel Activator Drugs: Mechanism of Action, Pharmacological Properties, and Therapeutic Potential," *Medicinal Research Reviews*, vol. 12, No. 2, 1992, pp. 73–148.
Masuda, Yukinori et al., "Potassium channel opening properties of a novel compound, NIP–121, cromakalim and nicorandil in rat aorta and portal vein," *European Journal of Pharmacology*, vol. 195, No. 3, 1991, pp. 323–331.
Masuda, Y. et al., "The Antihypertensive Property of NIP–121, A Novel Potassium Channel Opener in Rats," *Journal of Cardiovascular Pharmacology*, vol. 18, No. 2, 1991, pp. 190–197.
Shigenobu, Koki et al., Action Potential Shortening and Negative Inotropic Effects of a Novel Potassium Channel Opener, NIP–121, as Compared with Cromakalim in Guinea Pig Ventricular Myocardium, *Japan J. Pharmacol.*, vol. 57, No. 1, 1991, pp. 117–121.
Yamashita, Toru et al., "Cardiovascular Pharmacology of NIP–121, A Potassium Channel Opener," *Cardiovascular Drug Reviews*, vol. 13, No. 1, pp. 86–101, 1995.
Chiryougaku, *Biomed. Ther.*, vol. 16, No. 1, 1986, pp. 96–97.

*Primary Examiner*—Keith D. MacMillan
*Attorney, Agent, or Firm*—Oliff & Berridge, PLC

[57] ABSTRACT

Disclosed are cardiotonic medicines containing, as the active ingredient, at least one of compounds of formula (I) and their pharmacologically acceptable salts when they form salts.

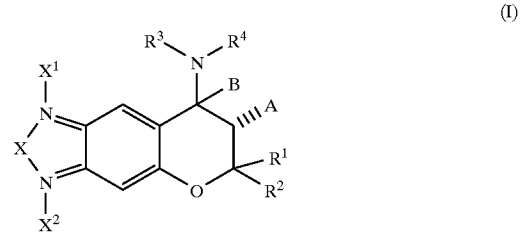

(I)

wherein $X^1$ and $X^2$ do not exist or represents an oxygen atom; A represents OH or a $C_1$–$C_4$ acyloxy group; B represents a hydrogen atom or may form a chemical bond along with A; X is an oxygen atom, nitrogen, sulfur, etc.; $R^1$ and $R^2$ each represents a hydrogen atom, a $C_1$–$C_4$ alkyl group, etc.; $R^3$ and $R^4$ each represents a hydrogen atom, a $C_1$–$C_4$ alkyl group, etc., or they may together form a 1,4-butylene or 1,5-pentylene group. The compounds have a strong activity of reinforcing the contraction of cardiac muscles and a strong activity of reducing the rate of heart beats. As they are not toxic, they are useful as cardiotonic medicines.

6 Claims, No Drawings

MEDICINES FOR CARDIAC INSUFFICIENCY

This Application is a 371 of PCT/JP94/00544, filed Apr. 1, 1994.

TECHNICAL FIELD

The present invention relates to the use of pharmaceutically active benzopyran derivatives as a medicine for cardiac insufficiency of mammals including human beings.

BACKGROUND ART

Japanese Patent Application Laid-Opens No. Hei 2-4791, No. Hei 2-49788, No. Hei 2-152974 and No. Hei 5-43432, U.S. Pat. No. 4,900,752, European Patent No. 327,127 and EP-A-492,391 have disclosed the possibility that benzopyran derivatives are usable as a medicine for curing disorders of cardiovascular systems such as hypertension, angina pectoris, arrhythmia, etc. and also as a hair growth stimulants for curing alopecia. However, they do not refer to the possibility that the derivatives might be usable as a medicine for curing diseases associated with cardiac insufficiency.

DISCLOSURE OF INVENTION

The present inventors intensively studied and investigated various benzopyran derivatives so as to obtain those having a low potassium channel opening activity while having no cardio-suppressing activity but rather having an activity of increasing constriction of heart and, as a result, have found that the compounds of the following formula (I) have a strong cardiotonic activity. On the basis of this finding, the present invention has been completed.

Specifically, the present invention is directed to the compounds of the following formula (I), their optical isomers, their stereoisomers and their pharmaceutically acceptable salts when they may form salts.

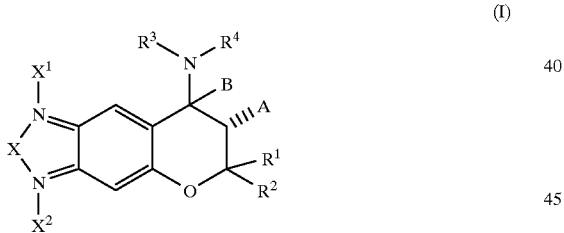

(I)

wherein $X^1$ and $X^2$ do not exist or represent an oxygen atom; X represents an oxygen atom, a sulfur atom, a nitrogen atom (said nitrogen atom is unsubstituted or substituted by a hydrogen atom or a $C_1$–$C_4$ alkyl group), C(O), C(S), or C(N—CN); A represents a hydrogen atom, a hydroxyl group, or $OC(O)R^5$ (in which $R^5$ represents a $C_1$–$C_4$ alkyl group), or may form a single bond together with B;

B represents a hydrogen atom, or may form a single bond together with A;

$R^1$ and $R^2$ are the same or different from each other and represents hydrogen atom or a $C_1$–$C_4$ alkyl group, or $R^1$ and $R^2$ may together form a 1,4-butylene or 1,5-pentylene group which is unsubstituted or substituted by $C_1$–$C_4$ alkyl group(s);

$R^3$ and $R^4$ are the same or different from each other and represent a hydrogen atom, a $C_1$–$C_6$ alkyl group {said alkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_2$–$C_6$ alkenyl group {said alkenyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_2$–$C_6$ alkynyl group {said alkynyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_3$–$C_6$ cycloalkyl group {said cycloalkyl group is unsubstituted or substituted by one or more substituents selected from a halogen atom, a carboxyl group, a $C_2$–C5 alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a phenyl group (which is unsubstituted or substituted by one or more substituents selected from a halogen atom, a hydroxyl group, and a $C_1$–$C_4$ alkoxy group), or C(=Y)$ZR^6$ [where Y represents an oxygen atom, a sulfur atom or $NR^7$ (in which $R^7$ represents a hydrogen atom, a cyano group, a nitro group, a $C_1$–$C_4$ alkyl group, a $C_1$–$C_4$ alkoxy group or $CO_2R^8$ ($R^8$ represent a $C_1$–$C_4$ alkyl group)); Z represents an oxygen atom, a sulfur atom or $NR^9$ (in which $R^9$ represents a hydrogen atom, a $C_1$–$C_6$ alkyl group {said alkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_2$–$C_6$ alkenyl group {said alkenyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_2$–$C_6$ alkynyl group {said alkynyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–C4 alkoxy group), a formyl group, a cyano group and a nitro group}, a $C_3$–$C_6$ cycloalkyl group {said cycloalkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, or a phenyl group (which is unsubstituted or substituted by one or more substituents selected from a halogen atom, a hydroxyl group and a $C_1$–$C_4$ alkoxy group)); and $R^6$ represents a hydrogen atom, a $C_1$–$C_8$ alkyl group {said alkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_2$–$C_5$ alkenyl group (said alkenyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_2$–$C_6$ alkynyl group {said alkynyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_3$–$C_6$ cycloalkyl group {said cycloalkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, or a phenyl group (which is unsubstituted or substituted by one or more substituents selected from a halogen atom, a hydroxyl group and a $C_1$–$C_4$ alkoxy group))]; or $R^3$ and $R^4$ may together form a 1,4-butylene or 1,5-pentylene group {said 1,4-butylene group and 1,5-pentylene group are unsubstituted or substituted by one or more substituents selected from a $C_1$–$C_4$ alkyl group, a phenyl group (which is unsubstituted or substituted by one or more substituents selected from a halogen atom, a hydroxyl group and a $C_1$–$C_4$ alkoxy group), a halogen atom, $OR^{10}$ (where $R^{10}$ represents a hydrogen atom, a $C_1$–$C_4$ alkyl group, $COR^{11}$ ($R^{11}$ represents a $C_1$–$C_4$ alkyl group), a nitro group, $SO_3H$ or $PO_3H_2$)}; or $R^3$ and $R^4$ may together form $(CH_2)_mX^4(CH_2)_1$ [in which m and 1 each represent 1, 2 or 3 while the sum of them is 3, 4 or 5; $X^4$ represents an oxygen atom, a sulfur atom, or $NR^{12}$ {in which $R^{12}$ represents a hydrogen atom, a $C_1$–$C_4$ alkyl group, or a phenyl group (which is unsubstituted or substituted by one or more substituents selected from a halogen atom, a hydroxyl group and a $C_1$–$C_4$ alkoxy group)}]; or $R^3$ and $R^4$ may together form $(CH_2)_nZC(=Y)$ (in which n represents 2, 3 or 4; and Z and Y have the same meanings as defined above).

The present invention relates to medicines for cardiac insufficiency, containing these compounds as active ingredients.

The compounds shown in the formula (I) of present invention reinforces constraction of cardiac muscles and are useful for improving cardiac functions. They are therefore usable as a medicine for treating cardiac insufficiency. They not only have a cardiotonic activity, but also have a strong activity of reducing the rate of heart beats.

The substituents in the compounds of formula (I) will be explained in more detail hereunder.

In this specification, "n-" means normal; "i-" means iso; "sec-" means secondary; "t-" means tertiary-; "c-" means cyclo-; "Me" means methyl; "Et" means ethyl; "Pr" means propyl; "Bu" means butyl; "Pen" means pentyl; "Hex" means hexyl; and "Ph" means phenyl.

Examples of $R^1$ and R2 include a hydrogen atom, Me, Et, n-Pr, i-Pr, n-Bu, i-Bu, sec-Bu and t-Bu. $R^1$ and $R^2$ may together form $(CH_2)_4$ or $(CH_2)_5$ to give spiro-rings.

Examples of A include OH, OC(O)Me, OC(O)Et, OC(O)-n-Pr, OC(O)-i-Pr, OC(O)-n-Bu, OC(O)-i-Bu, OC(O)-sec-Bu, OC(O)-t-Bu, etc.

A and B may together form a single bond.

Examples of X include an oxygen atom, a sulfur atom, C(O), C(S), NH, NMe, NEt, N-n-Pr, N-i-Pr, N-c-Pr, N-n-Bu, N-i-Bu, N-sec-Bu, N-t-Bu, etc.

Examples of $R^3$ and $R^4$ include a hydrogen atom, Me, Et, n-Pr, i-Pr, c-Pr, n-Bu, i-Bu, sec-Bu, t-Bu, n-Pen, c-Pen, n-Hex, c-Hex, Ph, benzyl, para-chlorophenylmethyl, para-fluorophenylmethyl, para-bromophenylmethyl, phenylethyl, para-chlorophenylethyl, para-fluorophenylethyl, para-bromophenylethyl, $CH_2CO_2H$, $CH_2CO_2Me$, $CH_2CO_2Et$, $(CH_2)_2CO_2Me$, $(CH_2)_2CO_2Et$, $(CH_2)_2CH(OMe)_2$, $(CH_2)_2CH(OEt)_2$, $(CH_2)_3OH$, $(CH_2)_3OMe$, $(CH_2)_3OEt$, $(CH_2)_3Cl$, $(CH_2)_3Br$, $(CH_2)_3F$, $(CH_2)_3CO_2H$, $(CH_2)_3CO_2Me$, $(CH_2)_3CO_2Et$, $(CH_2)_3CH(Me)_2$, $(CH_2)_3CH(Et)_2$, C(O)OMe, C(O)OEt, C(O)O-n-Pr, C(O)O-i-Pr, C(O)O-c-Pr, C(O)O-n-Bu, C(O)O-i-Bu, C(O)O-sec-Bu, C(O)O-t-Bu, C(O)O-n-Pen, C(O)O-c-Pen, C(O)O-n-Hex, C(O)O-c-Hex, C(O)O$(CH_2)_2Cl$, C(O)O$(CH_2)_2Br$, C(O)O$(CH_2)_3Cl$, C(O)O$(CH_2)_3Br$, C(O)OPh, C(O)OCH$_2$Ph, C(O)NHMe, C(O)NHEt, C(O)NH-n-Pr, C(O)NH-i-Pr, C(O)NH-c-Pr, C(O)NH-n-Bu, C(O)NH-i-Bu, C(O)NH-sec-Bu, C(O)NH-t-Bu, C(O)NH-n-Pen, C(O)NH-c-Pen, C(O)NH-n-Hex, C(O)NH-c-Hex, C(O)NH$(CH_2)_2Cl$, C(O)NH$(CH_2)_2Br$, C(O)NH$(CH_2)_3Cl$, C(O)NH$(CH_2)_3Br$, C(O)NHPh, C(O)NHCH$_2$Ph, C(O)NHC(O)CCl$_3$, C(S)NHMe, C(S)NHEt, C(S)NH-n-Pr, C(S)NH-i-Pr, C(S)NH-c-Pr, C(S)NH-n-Bu, C(S)NH-i-Bu, C(S)NH-sec-Bu, C(S)NH-t-Bu, C(S)NH-n-Pen, C(S)NH-c-Pen, C(S)NH-n-Hex, C(S)NH-c-Hex, C(S)NH$(CH_2)_2Cl$, C(S)NH$(CH_2)_2Br$, C(S)NH$(CH_2)_3Cl$, C(S)NH$(CH_2)_3Br$, C(S)NHPh, C(S)NHCH$_2$Ph, C(N—CN)NHMe, C(N—CN)NHEt, C(N—CN)NH-n-Pr, C(N—CN)NH-i-Pr, C(N—CN)NH-c-Pr, C(N—CN)NH-n-Bu, C(N—CN)NH-i-Bu, C(N—CN)NH-sec-Bu, C(N—CN)NH-t-Bu, C(N—CN)NH-n-Pen, C(N—CN)NH-c-Pen, C(N—CN)NH-n-Hex, C(N—CN)NH-c-Hex, C(N—CN)NH$(CH_2)_2Cl$, C(N—CN)NH$(CH_2)_2Br$, C(N—CN)NH$(CH_2)_3Cl$, C(N—CN)NH$(CH_2)_3Br$, C(N—CN)NHPh, C(N—CN)NHCH$_2$Ph, or the following Q1 to Q36 in which nitrogen atoms to which $R^3$ and $R^4$ and these substituents are together bound.

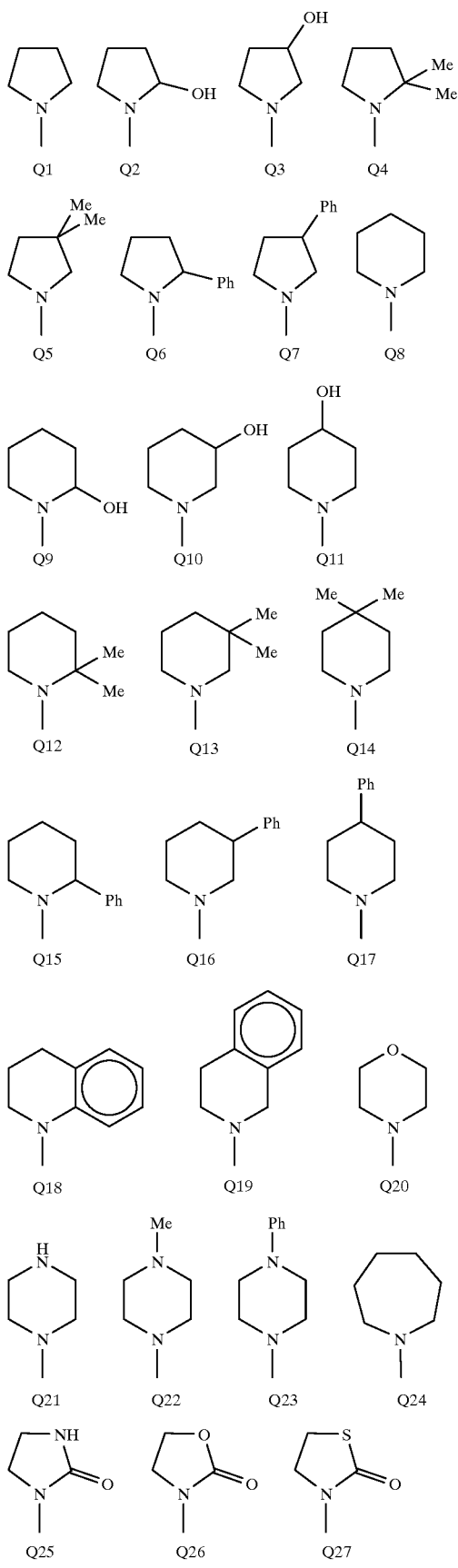

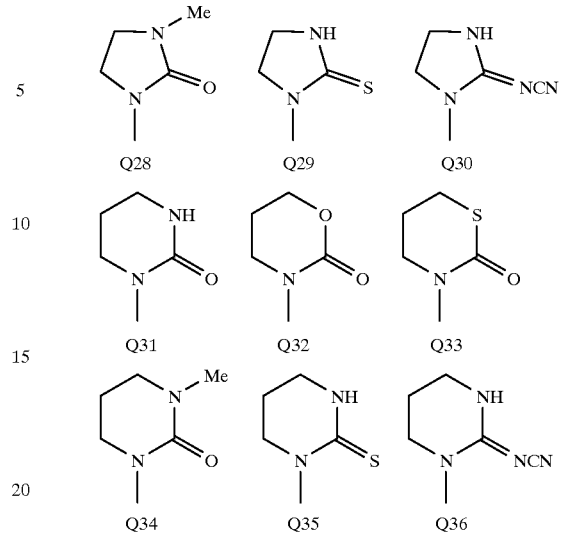

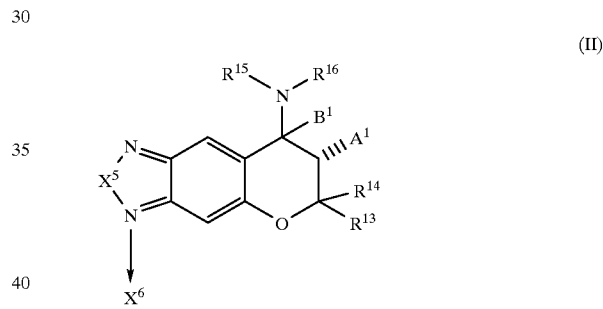

Among the medicines for cardiac insufficiency of the present invention, the preferable one is a medicine for cardiac insufficiency containing, as the active ingredient, at least one of compounds of the formula (II), their optical isomers, their stereoisomers and their pharmacologically acceptable salts when they may form salts:

$$\text{(II)}$$

wherein $X^6$ does not exist or represents an oxygen atom;

$X^5$ represents an oxygen atom, a sulfur atom, or a nitrogen atom (said nitrogen atom is unsubstituted or substituted by a hydrogen atom or a $C_1$–$C_4$ alkyl group);

$A^1$ represents a hydrogen atom, a hydroxyl group, or $OC(O)R^{17}$ (in which $R^{17}$ represents a $C_1$–$C_4$ alkyl group);

$B^1$ represents a hydrogen atom;

$R^{13}$ and $R^{14}$ are the same or different each other and represent a hydrogen atom or a $C_1$–$C_4$ alkyl group;

$R^{15}$ and $R^{16}$ are the same or different to each other and represent a hydrogen atom, a $C_1$–$C_6$ alkyl group {said alkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_3$–$C_6$ cycloalkyl group {said cycloalkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a phenyl group (which is unsubstituted or substituted by one or more substituents selected from a halogen atom, a hydroxyl group and a $C_1$–$C_4$ alkoxy group), or $c(=Y^1)Z^1 R^{18}$ [in which $Y^1$ represents an oxygen atom, a sulfur atom or $NR^{19}$ (in which $R^{19}$ represents a hydrogen atom, a cyano group, a nitro group, a $C_1$–$C_4$ alkyl group or a $C_1$–$C_4$ alkoxy group); $Z^1$ represents an oxygen atom, a sulfur atom or $NR^{20}$ (in which $R^{20}$ represents a hydrogen atom, a $C_1$–$C_6$ alkyl group {said alkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_3$–$C_6$ cycloalkyl group {said cycloalkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, or a phenyl group (which is unsubstituted or substituted by one or more substituents selected from a halogen atom, a hydroxyl group and a $C_1$–$C_4$ alkoxy group)); and $R^{18}$ represents a hydrogen atom, a $C_1$–$C_8$ alkyl group {said alkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, a $C_3$–$C_6$ cycloalkyl group {said cycloalkyl group is unsubstituted or substituted by one or more substituents selected from a halogen atom, a carboxyl group, a $C_2$–$C_5$ alkoxycarbonyl group, a hydroxyl group, a $C_1$–$C_4$ alkoxy group, $CH(OR)_2$ (in which R represents a $C_1$–$C_4$ alkyl group), a phenyl group (which is unsubstituted or substituted by one or more substituents selected from a halogen atom, a hydroxyl group and a $C_1$–$C_4$ alkoxy group), a formyl group, a cyano group and a nitro group}, or a phenyl group (which is unsubstituted or substituted by one or more substituents selected from a halogen atom, a hydroxyl group and a $C_1$–$C_4$ alkoxy group)]; or $R^{15}$ and $R^{16}$ may together form a 1,4-butylene or 1,5-pentylene group {said butylene and said pentylene are unsubstituted or substituted by one or more substituents selected from a $C_1$–$C_4$ alkyl group, a phenyl group (which is unsubstituted or substituted by one or more substituents selected from a halogen atom, a hydroxyl group and a $C_1$–$C_4$ alkoxy group), a halogen atom and $OR^{21}$ (in which $R^{21}$ represents a hydrogen atom, a $C_1$–$C_4$ alkyl group, $COR^{22}$ (in which $R^{22}$ represents a $C_1$–$C_4$ alkyl group), a nitro group, $SO_3H$ or $PO_3H_2$)}; or $R^{15}$ and $R^{16}$ may together form $(CH_2)_o X^7 (CH_2)_p$ [in which o and p each is an integer of 1, 2 or 3 while the sum of them is 3, 4 or 5; $X^7$ represents an oxygen atom, a sulfur atom, or $NR^{23}$ {in which $R^{23}$ represents a hydrogen atom, a $C_1$–$C_4$ alkyl group, or a phenyl group (which is unsubstituted or substituted by one or more substituents selected from a halogen atom, a hydroxyl group and a $C_1$–$C_4$ alkoxy group)}]; or $R^{15}$ and $R^{16}$ may together form $(CH_2)_Q Z^1 C(=Y^1)$ (in which Q represents an integer of 2, 3 or 4; and $Z^1$ and $Y^1$ have the same meanings as defined above).

The above-mentioned medicines for cardiac insufficiency in which $R^{15}$ in formula (II) represents a hydrogen atom, and $R^{16}$ represents $C(=Y^2)NHR^{24}$ (in which $Y^2$ represents an oxygen atom, a sulfur atom or N—CN; and $R^{24}$ represents a phenyl group, a benzyl group or a $C_1$–$C_8$ alkyl group which may be branched) are further preferable.

The medicines for cardiac insufficiency in which $R^{15}$ and $R^{16}$ in formula (II) together form $(CH_2)_k NHC(=Y^3)$ (in which k is an integer of 2, 3 or 4; and $Y^3$ represents an oxygen atom, a sulfur atom or N—CN) are one of further preferable ones.

The medicines for cardiac insufficiency in which $R^{15}$ and $R^{16}$ in formula (II) simultaneously represents $C_1$–$C_6$ alkyl groups are one of further preferable ones.

The medicines for cardiac insufficiency in which $R^{15}$ and $R^{16}$ in formula (II) together form $(CH_2)_4$ or $(CH_2)_5$ are one of further preferable ones.

Examples of the compounds of formula (I) of the present invention are mentioned below, in which "—" indicates the absence of $X^1$ and/or $X^2$. Qn has the meaning as defined above. $(Qn=(R^3—)(R^4—)N—)$

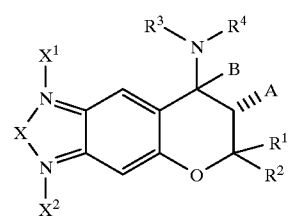

(I)

TABLE 1

| No. | X | $X^1$ | $X^2$ | A | B | $R^1$ | $R^2$ | $R^3$ | $R^4$ |
|---|---|---|---|---|---|---|---|---|---|
| 1 | O | — | O | OH | H | Me | Me | Et | Et |
| 2 | O | — | O | OH | H | Me | Me | ($R_3$—)($R_4$—)N— = Q8 | |
| 3 | O | — | — | OH | H | Me | Me | ($R_3$—)($R_4$—)N— = Q8 | |
| 4 | O | — | — | OH | H | Me | Me | ($R_3$—)($R_4$—)N— = Q1 | |
| 5 | O | — | — | OH | H | Me | Me | H | Me |

TABLE 1-continued

| No. | X | X¹ | X² | A | B | R¹ | R² | R³ | R⁴ |
|---|---|---|---|---|---|---|---|---|---|
| 6 | O | — | — | OH | H | Me | Me | H | CH₂Ph(p-F) |
| 7 | O | — | — | OH | H | Me | Me | H | CH₂Ph |
| 8 | O | — | — | OH | H | Me | Me | Me | CH₂Ph |
| 9 | O | — | — | OH | H | Me | Me | H | n-Hex |
| 10 | O | — | — | OH | H | Me | Me | (R₃—)(R₄—)N— = Q22 | |
| 11 | O | — | — | OH | H | Me | Me | (R₃—)(R₄—)N— = Q21 | |
| 12 | O | — | — | OH | H | Me | Me | (R₃—)(R₄—)N— = Q23 | |
| 13 | O | — | — | OH | H | Me | Me | (R₃—)(R₄—)N— = Q17 | |
| 14 | O | — | — | OH | H | Me | Me | (R₃—)(R₄—)N— = Q19 | |
| 15 | O | — | — | OH | H | Me | Me | (R₃—)(R₄—)N— = Q20 | |
| 16 | O | — | — | OH | H | Me | Me | H | (CH₂)₃OMe |
| 17 | O | — | — | OH | H | Me | Me | H | (CH₂)₃CO₂Et |
| 18 | O | — | — | OH | H | Me | Me | H | CH₂CO₂Et |
| 19 | O | — | — | OH | H | Me | Me | H | (CH₂)₃Cl |
| 20 | O | — | — | OH | H | Me | Me | H | (CH₂)₂OH |
| 21 | O | — | — | OH | H | Me | Me | H | H |
| 22 | O | — | — | OH | H | Me | Me | H | C(O)NHMe |
| 23 | O | — | — | OH | H | Me | Me | H | C(S)NHMe |
| 24 | O | — | — | OH | H | Me | Me | H | C(O)NHPh |
| 25 | O | — | — | OH | H | Me | Me | H | C(O)NHC(O)CCl₂ |
| 26 | O | — | — | OH | H | Me | Me | H | C(O)NH(CH₂)₃Cl |
| 27 | O | — | — | OH | H | Me | Me | H | C(O)NH(CH₂)₂Cl |
| 28 | O | — | — | OH | H | Me | Me | H | C(O)NH-i-Pr |
| 29 | O | — | — | OH | H | Me | Me | H | C(O)OEt |
| 30 | O | — | — | OH | H | Me | Me | H | C(O)O(CH₂)₂Cl |
| 31 | O | — | — | OH | H | Me | Me | (R₃—)(R₄—)N— = Q26 | |
| 32 | O | — | — | OH | H | Me | Me | (R₃—)(R₄—)N— = Q25 | |
| 33 | O | — | — | OH | H | Me | Me | H | C(O)NH-c-Hex |
| 34 | O | — | — | OH | H | Me | Me | H | C(O)NH-t-Bu |
| 35 | O | — | — | OH | H | Me | Me | H | C(O)OMe |
| 36 | O | — | — | OH | H | Me | Me | H | C(O)NH-t-Bu |
| 37 | O | — | — | OH | H | Me | Me | (R₃—)(R₄—)N— = Q31 | |
| 38 | O | — | — | OH | H | Me | Me | H | C(O)O(CH₂)₃Cl |
| 39 | O | — | — | OH | H | Me | Me | (R₃—)(R₄—)N— = Q32 | |
| 40 | O | — | O | OC(O)Me | H | Me | Me | Et | Et |
| 41 | O | — | — | OH | H | Me | Me | Et | Et |
| 42 | O | — | — | OC(O)Me | H | Me | Me | Et | Et |
| 43 | O | — | — | OC(O)Me | H | Me | Me | (R₃—)(R₄—)N— = Q8 | |
| 44 | O | — | — | OH | H | Me | Me | H | (CH₂)₃CH(OEt)₂ |
| 45 | O | — | — | OH | H | Me | Me | (R₃—)(R₄—)N— = Q2 | |
| 46 | O | — | — | OH | H | Me | Me | H | (CH₂)₃CO₂H |
| 47 | O | — | — | OC(O)Me | H | Me | Me | H | H |
| 48 | O | — | — | OH | H | Et | Et | (R₃—)(R₄—)N— = Q8 | |
| 49 | O | — | — | OH | H | Et | Et | H | H |
| 50 | O | — | — | OH | H | Et | Et | H | C(O)NHMe |
| 51 | O | — | — | OC(O)Me | H | Et | Et | H | H |
| 52 | O | — | — | OH | H | Me | Me | H | C(N—CN)NH-t-Bu |
| 53 | NH | — | — | OH | H | Me | Me | (R₃—)(R₄—)N— = Q8 | |
| 54 | NH | — | — | OH | H | Me | Me | (R₃—)(R₄—)N— = Q1 | |
| 55 | NH | — | — | OH | H | Me | Me | Et | Et |
| 56 | S | — | — | OH | H | Me | Me | (R₃—)(R₄—)N— = Q8 | |
| 57 | S | — | — | OH | H | Me | Me | (R₃—)(R₄—)N— = Q1 | |
| 58 | S | — | — | OH | H | Me | Me | Et | Et |
| 59 | O | — | — | OH | H | Me | Me | (R₃—)(R₄—)N— = Q3 | |
| 60 | O | — | — | OH | H | Me | Me | (R₃—)(R₄—)N— = Q4 | |
| 61 | O | — | — | OH | H | Me | Me | (R₃—)(R₄—)N— = Q5 | |
| 62 | O | — | — | OH | H | Me | Me | (R₃—)(R₄—)N— = Q6 | |
| 63 | O | — | — | OH | H | Me | Me | (R₃—)(R₄—)N— = Q7 | |
| 64 | O | — | — | OH | H | Me | Me | (R₃—)(R₄—)N— = Q9 | |
| 65 | O | — | — | OH | H | Me | Me | (R₃—)(R₄—)N— = Q10 | |
| 66 | O | — | — | OH | H | Me | Me | (R₃—)(R₄—)N— = Q11 | |
| 67 | O | — | — | OH | H | Me | Me | (R₃—)(R₄—)N— = Q12 | |
| 68 | O | — | — | OH | H | Me | Me | (R₃—)(R₄—)N— = Q13 | |
| 69 | O | — | — | OH | H | Me | Me | (R₃—)(R₄—)N— = Q14 | |
| 70 | O | — | — | OH | H | Me | Me | (R₃—)(R₄—)N— = Q15 | |
| 71 | O | — | — | OH | H | Me | Me | (R₃—)(R₄—)N— = Q16 | |
| 72 | O | — | — | OH | H | Me | Me | (R₃—)(R₄—)N— = Q18 | |
| 73 | O | — | — | OH | H | Me | Me | (R₃—)(R₄—)N— = Q24 | |
| 74 | O | — | — | OH | H | Me | Me | (R₃—)(R₄—)N— = Q27 | |
| 75 | O | — | — | OH | H | Me | Me | (R₃—)(R₄—)N— = Q28 | |
| 76 | O | — | — | OH | H | Me | Me | (R₃—)(R₄—)N— = Q29 | |
| 77 | O | — | — | OH | H | Me | Me | (R₃—)(R₄—)N— = Q30 | |
| 78 | O | — | — | OH | H | Me | Me | (R₃—)(R₄—)N— = Q38 | |
| 79 | O | — | — | OH | H | Me | Me | (R₃—)(R₄—)N— = Q34 | |
| 80 | O | — | — | OH | H | Me | Me | (R₃—)(R₄—)N— = Q35 | |
| 81 | O | — | — | OH | H | Me | Me | (R₃—)(R₄—)N— = Q36 | |
| 82 | O | — | — | OH | H | Me | Me | Me | Me |

TABLE 1-continued

| No. | X | X¹ | X² | A | B | R¹ | R² | R³ | R⁴ |
|---|---|---|---|---|---|---|---|---|---|
| 83 | O | — | — | OH | H | Me | Me | n-Pr | n-Pr |
| 84 | O | — | — | OH | H | Me | Me | i-Pr | i-Pr |
| 85 | O | — | — | OH | H | Me | Me | c-Pr | c-Pr |
| 86 | O | — | — | OH | H | Me | Me | n-Bu | n-Bu |
| 87 | O | — | — | OH | H | Me | Me | i-Bu | i-Bu |
| 88 | O | — | — | OH | H | Me | Me | sec-Bu | sec-Bu |
| 89 | O | — | — | OH | H | Me | Me | t-Bu | t-Bu |
| 90 | O | — | — | OH | H | Me | Me | n-Pen | n-Pen |
| 91 | O | — | — | OH | H | Me | Me | n-Hex | n-Hex |
| 92 | O | — | — | OH | H | Me | Me | c-Pen | c-Pen |
| 93 | O | — | — | OH | H | Me | Me | c-Hex | c-Hex |
| 94 | O | — | — | OH | H | Me | Me | Ph | Ph |
| 95 | O | — | — | OH | H | Me | Me | $CH_2Ph$ | $CH_2Ph$ |
| 96 | O | — | — | OH | H | Me | Me | H | C(S)NHEt |
| 97 | O | — | — | OH | H | Me | Me | H | C(S)NH-n-Pr |
| 98 | O | — | — | OH | H | Me | Me | H | C(S)NH-i-Pr |
| 99 | O | — | — | OH | H | Me | Me | H | C(S)NH-c-Pr |
| 100 | O | — | — | OH | H | Me | Me | H | C(S)NH-n-Bu |
| 101 | O | — | — | OH | H | Me | Me | H | C(S)NH-i-Bu |
| 102 | O | — | — | OH | H | Me | Me | H | C(S)NH-sec-Bu |
| 103 | O | — | — | OH | H | Me | Me | H | C(S)NH-n-Pen |
| 104 | O | — | — | OH | H | Me | Me | H | C(S)NH-c-Pen |
| 105 | O | — | — | OH | H | Me | Me | H | C(S)NH-n-Hex |
| 106 | O | — | — | OH | H | Me | Me | H | C(S)NH-c-Hex |
| 107 | O | — | — | OH | H | Me | Me | H | C(S)NHPh |
| 108 | O | — | — | OH | H | Me | Me | H | $C(S)NHCH_2Ph$ |
| 109 | O | — | — | OH | H | Me | Me | H | C(N—CN)NHMe |
| 110 | O | — | — | OH | H | Me | Me | H | C(N—CN)NHEt |
| 111 | O | — | — | OH | H | Me | Me | H | C(N—CN)NHEt |
| 112 | O | — | — | OH | H | Me | Me | H | C(N—CN)NH-n-Pr |
| 113 | O | — | — | OH | H | Me | Me | H | C(N—CN)NH-i-Pr |
| 114 | O | — | — | OH | H | Me | Me | H | C(N—CN)NH-c-Pr |
| 115 | O | — | — | OH | H | Me | Me | H | C(N—CN)NH-n-Bu |
| 116 | O | — | — | OH | H | Me | Me | H | C(N—CN)NH-i-Bu |
| 117 | O | — | — | OH | H | Me | Me | H | C(N—CN)NH-sec-Bu |
| 118 | O | — | — | OH | H | Me | Me | H | C(N—CN)NH-n-Pen |
| 119 | O | — | — | OH | H | Me | Me | H | C(N—CN)NH-c-Pen |
| 120 | O | — | — | OH | H | Me | Me | H | C(N—CN)NH-n-Hex |
| 121 | O | — | — | OH | H | Me | Me | H | C(N—CN)NH-c-Hex |
| 122 | O | — | — | OH | H | Me | Me | H | C(N—CN)NH-Ph |
| 123 | O | — | — | OH | H | Me | Me | H | $C(N-CN)NH-NH_2Ph$ |
| 124 | O | — | — | OH | H | Me | Me | Me | n-Pr |
| 125 | O | — | — | OH | H | Me | Me | Et | n-Pr |
| 126 | O | — | — | OH | H | Me | Me | n-Pr | n-Bu |
| 127 | O | — | — | OH | H | Me | Me | n-Pr | n-Pen |
| 128 | O | — | — | OH | H | Me | Me | n-Pr | c-Pen |
| 129 | O | — | — | OH | H | Me | Me | Et | n-Hex |
| 130 | O | — | — | OH | H | Me | Me | Et | Ph |
| 131 | O | — | — | OH | H | Me | Me | n-Pr | $CH_2Ph$ |

The compounds of formula (I) of the present invention have asymmetric carbon atoms at the 3- and 4-positions in the pyran ring and therefore include opticallyly active substances based on the asymmetric carbon atoms. Such optically active substances may also be used in the present invention, like the racemic modifications. In addition, stereoisomers based on the 3- and 4-positions in the pyran ring may also be used. If the compounds may form salts, their pharmacologically acceptable salts may also be used as the active ingredients of the present invention.

Methods for producing the compounds of formula (I) of the present invention will be mentioned below.

Of the compounds of formula (I), compounds in which X is an oxygen atom and $R^3$ and $R^4$ do not simultaneously form $C(=Y)ZR^6$ are obtained, as shown by the following reaction scheme, by reacting a compound of formula (3) with a compound of formula (4) in an inert solvent. The compounds in which A represents OH are shown in formula (5). The compounds in which A forms a single bond together with B are shown by formula (6).

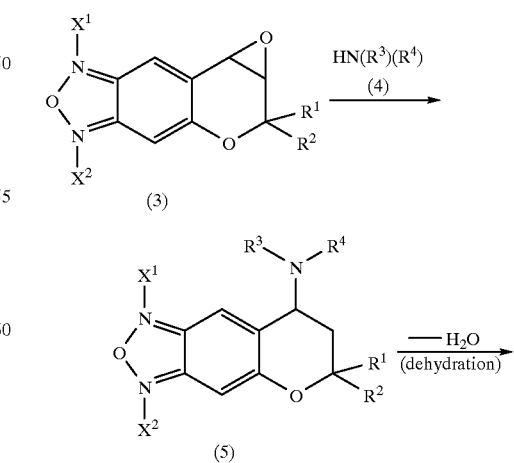

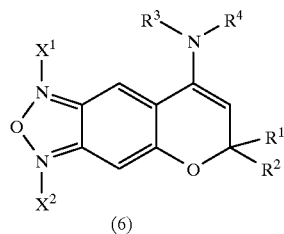

(6)

The solvent usable for the reaction of the compound (3) and the compound (4) includes, for example, sulfoxide solvents such as dimethylsulfoxide, amide solvents such as dimethylformamide and dimethylacetamide, ether solvents such as ethyl ether, dimethoxyethane and tetrahydrofuran, and alcohol solvents such as methanol, ethanol and isopropanol. Of these, preferred are alcohol solvents.

The reaction temperature of reacting the two compounds (3) and (4) may be from ice-cooled temperature to the reflux temperature for the reaction solvent used, preferably at the reflux temperature for the solvent used. If desired, the reaction may be conducted under pressure.

Regarding the molar ratio of the starting compounds, the ratio of compound (4)/compound (3)(by molar ratio) is within the range of from 0.5 to 2.0, preferably from 1.0 to 1.1.

Either the compound of formula (5) or the compound of formula (6) is obtained by the reaction, depending on the reaction conditions or the conditions for the post-treatment after the reaction which will be mentioned in detail hereunder. Precisely, the compound of formula (6) is obtained by reacting the compound of formula (3) and the compound of formula (4) in tetrahydrofuran in the presence of sodium hydride. However, the compound of formula (5) may also be obtained by the same reaction, depending on the reaction conditions (e.g., reaction time, reaction temperature, etc.).

As the case may be, the compound of formula (5) obtained by the reaction is often dehydrated, depending on the difference of the post-treatment of the compound formed by the reaction. For instance, when the reaction solution contains an acid or alkali and when it is directly heated and concentrated without removing the acid or alkali by rinsing, the compound formed in the reaction solution will often be dehydrated.

However, the dehydrating conditions are apt to be influenced by the kind of the compound formed, the reaction conditions and the conditions for the post-treatment.

Of the compounds of formula (I) of the present invention, the compounds in which X is an oxygen atom and either $R^3$ or $R^4$ represents $C(=Y)ZR^6$ are obtained according to the reaction scheme mentioned below, in which a compound of formula (3) is reacted with a compound of formula (7) in an inert solvent to give a compound of formula (8) and the compound of formula (8) is reacted with $R^6NCY$ ($R^6NCO$, $R^6NCS$) or $ClCO_2R^6$ to give a compound of formula (9) or (10).

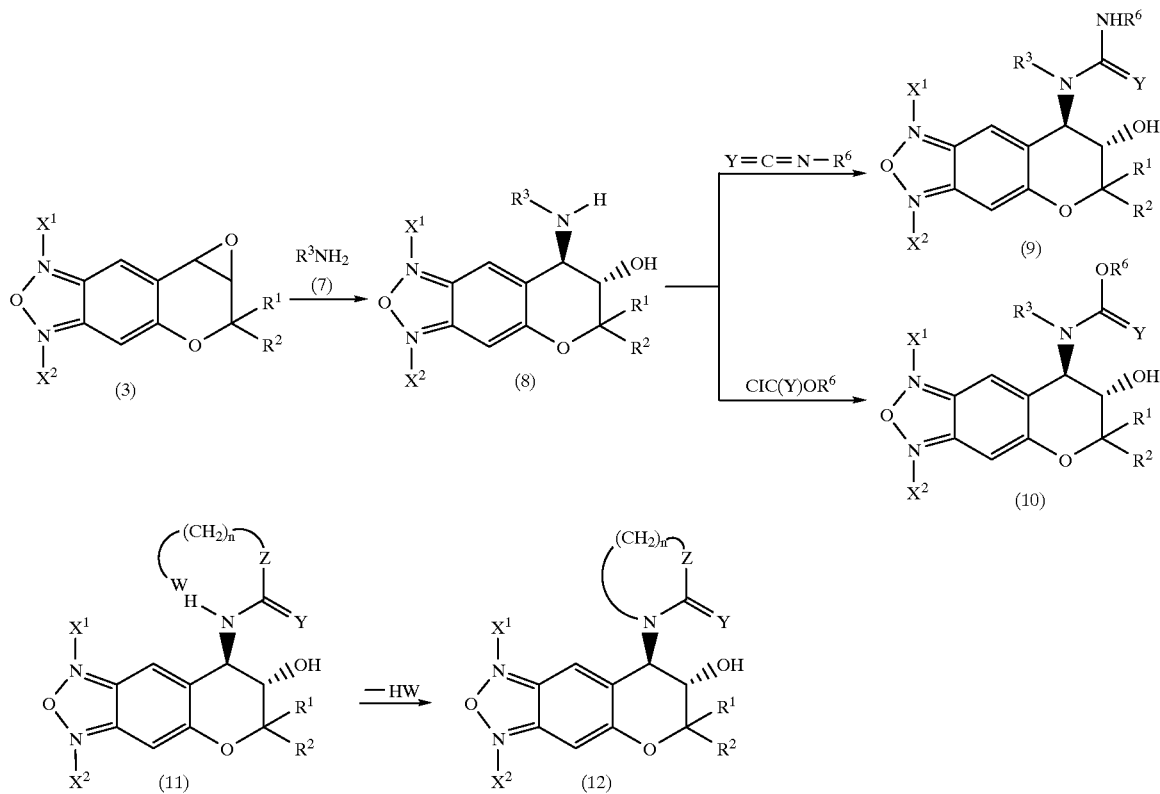

In the reaction schemes, Z represents N(R⁹) or an oxygen atom or sulfur atom; W represents a chlorine atom, a bromine atom, an iodine atom, a lower alkylsulfonate, a benzenesulfonate or a toluenesulfonate.

According to the reaction scheme mentioned above, a compound in which $R^3$ and $R^4$ together form a ring is obtained by cyclizing the compound represented by formula (11).

The starting compounds of the following formula (3):

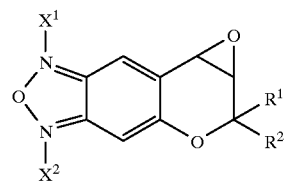

(3)

wherein $R^1$ and $R^2$ have the same definitions as those in formula (I), may be obtained according to the reaction scheme mentioned below. The whole flow for obtaining them are shown below.

with a reducing agent having an ability of removing an N-oxide type oxygen, such as typically sodium azide ($NaN_3$) or triethyl phosphite ($P(OEt)_3$), to give a compound which is represented by formula (3) and in which $X^1$ and $X^2$ are both absent (Compound 3($X^1$=$X^2$=-)). When Compound 3 ($X^1$=$X^2$=-) is treated with about one equivalent amount of a suitable peracid (e.g., m-chloroperbenzoic acid, hydrogen peroxide, peracetic acid—the same shall apply hereunder), then a compound which is represented by formula (3) and in which $X^1$ is an oxygen atom and $X^2$ is absent (Compound 3 ($X^1$=O, $X^2$=-)) is obtained. When more than one equivalent of the peracid is used in the reaction, then a compound of formula (3) in which $X^1$ and $X^2$ are both oxygen atoms (Compound 3 ($X^1$=$X^2$=O)) is obtained. The compound of formula (13) may be obtained by known methods (for example, refer to J.Med. Chem., 27, 1127(1987)).

Compound 3 ($X^1$=O, $X^2$=-) may also be obtained by treating a compound of formula (14):

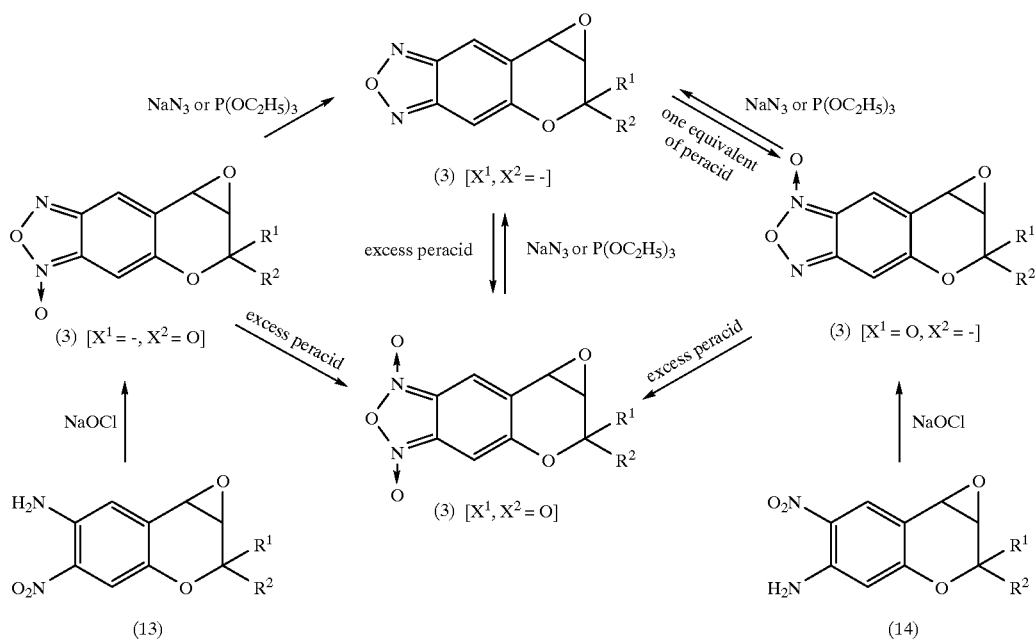

Precisely, a compound of formula (13):

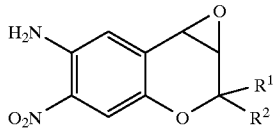

(13)

wherein $R^1$ and $R^2$ have the same definitions as those in formula (I), is treated with sodium hypochlorite (NaOCl) to give a compound which is represented by formula (3) and in which $X^1$ is absent and $X^2$ is an oxygen atom (Compound 3 ($X^1$=-, $X^2$=O)), the resulting compound is then reacted

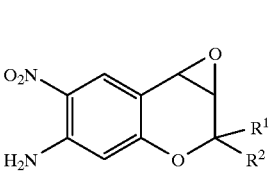

(14)

wherein $R^1$ and $R^2$ have the same definitions as those in formula (I), with sodium hypochlorite. The compound of formula (14) may be obtained by known methods (for example, refer to the above-mentioned literature). The solvent usable for the reaction of the compound (8) and the compound of Y=C=N—$R^6$ or ClC(O)O$R^6$ includes, for example, sulfoxide solvents such as dimethylsulfoxide, amide solvents such as dimethylformamide or dimethylacetamide, ether solvents such as ethyl ether, dimethoxyethane or tetrahydrofuran, and halogen compound solvents such as methylene chloride and chloroform. Of these, preferred are halogen compound solvents.

The reaction temperature may be from an ice-cooled temperature to the reflux temperature for the raction solvent used, preferably at the reflux temperature for the solvent used. If desired, the reaction may be conducted under pressure.

Regarding the molar ratio of the starting compounds, the ratio of compound (8)/Y=C=N—$R^6$ or ClC(O)$OR^6$ (by molar ratio) is within the range of from 0.5 to 2.0, preferably from 1.0 to 1.1.

Of the compounds of formula (I) of the present invention, compounds in which X is a sulfur atom or a nitrogen atom (which is unsubstituted or substituted by a hydrogen atom or a $C_1$–$C_9$ alkyl group) may be synthesized by a compound of formula (15) via three or four steps. The conversion of the compound of formula (15) into a compound of formula (17) is attained, for example, known methods described in Japanese Patent Application Laid-Open No. Sho 56-57785 and No. Sho 56-122 380. The compound of formula (17) is then subjected to conventional diazotation, for example, by treating it with sodium nitrite in an aqueous solution in the presence of an inorganic acid such as hydrochloric acid or sulfuric acid or an organic acid such as acetic acid, and thereafter cyclized under heat at 5 to 100° C., preferably at 50 to 100° C. to give a compound of formula (18) where X is a nitrogen atom.

A compound of formula (I) in which A and B together form a single bond may often be formed by merely heating the compound of formula (18). Therefore, the former may often be obtained during the synthesis reaction of the compound of formula (18) or during the post-treatment of the same. If desired, it may also be synthesized by dehydrating the compound of formula (18) with an acid anhydride such as benzoic anhydride or acetic anhydride or with a base such as potassium carbonate.

A compound of formula (I) in which X is an alkylamino group may be obtained by reacting the compound of formula (18) or its dehydrate with diazomethane or with an alkyl halide in the presence of potassium carbonate.

The compound of formula (17) may be reacted with thionylaniline in an inert solvent, such as benzene, toluene, xylene or dichlorobenzene, to give a compound of formula (20) in which X is a sulfur atom.

The reaction temperature for the reactions may be at 5 to 120° C., preferably 50 to 100° C.

A compound of formula (I) in which A and B together form a single bond may often be formed by merely heating the compound of formula (20). Therefore, the former may often be obtained during the synthesis reaction of the compound of formula (20) or during the post-treatment of the same. If desired, it may also be synthesized by dehydrating the compound of formula (20) with an acid anhydride such as benzoic anhydride or acetic anhydride or with a base such as potassium carbonate.

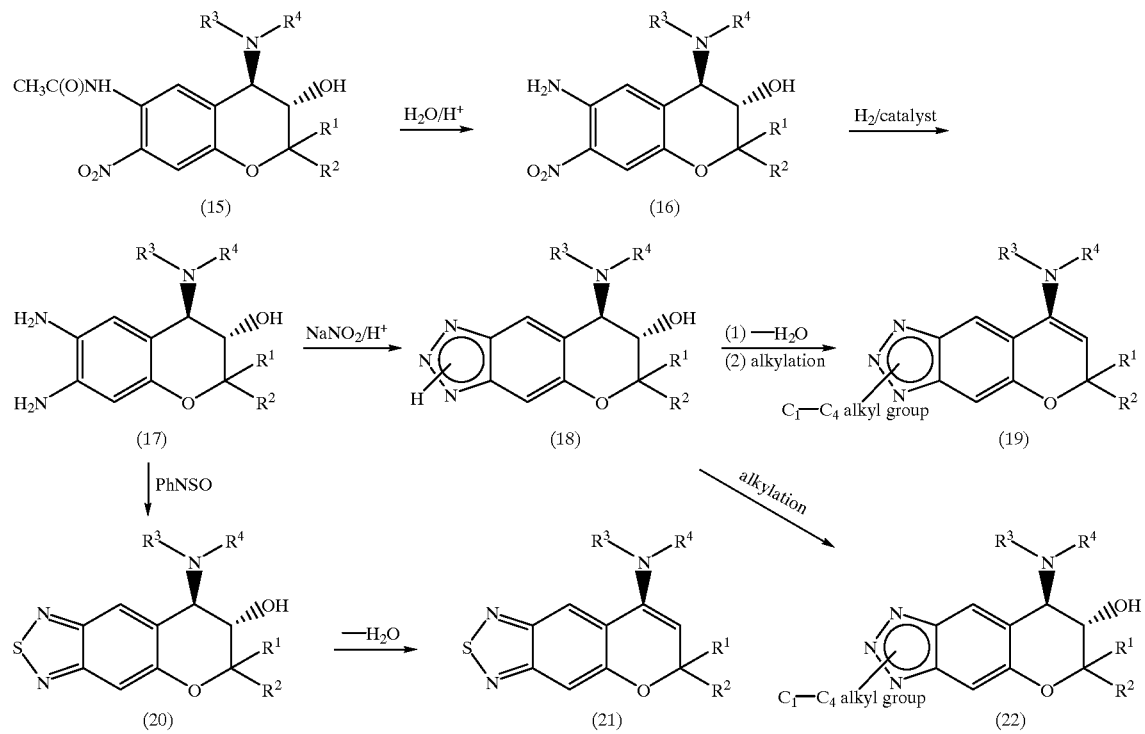

-continued

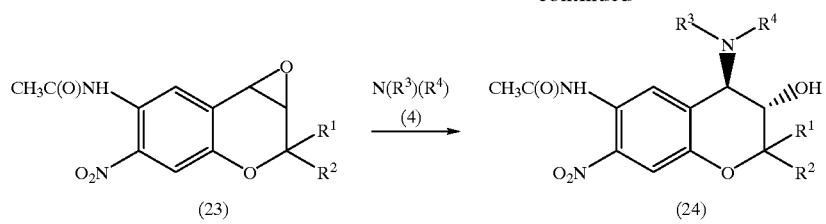

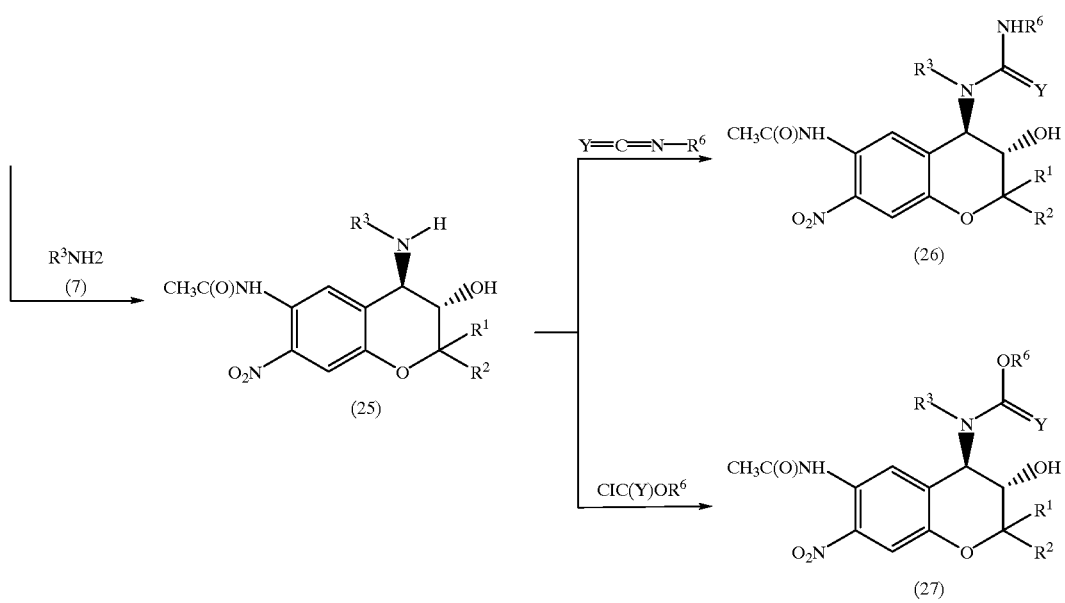

In these reaction schemes, Z represents $N(R^9)$ or an oxygen or sulfur atom; and W represents a chlorine atom, a bromine atom, an iodine atom, a lower alkylsulfonate, a benzenesulfonate or a toluenesulfonate.

Of the compounds of formula (15), a compound of formula (24) where $R^3$ and $R^4$ both do not represent $C(=Y)ZR^6$ ($R^3$ and $R^4$ in this case do not simulate aneously include $C(=Y)ZR^6$) may be obtained by reacting a compound of formula (23) and a compound of formula (4) in an inert solvent.

The solvent to be used for the reaction of the compound of formula (23) and the compound of formula (4) includes, for example, sulfoxide solvents such as dimethylsulfoxide, amide solvents such as dimethylformamide or dimethylacetamide, ether solvents such as ethyl ether, dimethoxyethane or tetrahydrofuran, and alcohol solvents such as methanol, ethanol or isopropanol. Of these , preferred are alcohol solvents.

The reaction temperature may be from the ice-cooled temperature to the reflux temperature of the reaction solvent used, temperature, the reaction temperature is preferably at the reflux temperature for the solvent used. If desired, the reaction may be conducted under pressure.

Regarding the molar ratio of the starting compounds, the ratio of compound (4)/compound (23) (by molar ratio) is within the range of from 0.5 to 2.0, preferably from 1.0 to 1.1.

Of the compounds of formula (15), compounds of formulae (26) and (27) in which either of $R^3$ and $R^4$ represents $C(=Y)ZR^6$ may be obtained according to the reaction scheme mentioned above, in which a compound of formula (23) is reacted with a compound of formula (7) in an inert solvent to give a compound of formula (25) and the resulting compound is reacted with $R^6NCY$ ($R^6NCO$, $R^6NCS$) or with $ClCO_2R^6$ to give a compound of formula (26) or (27).

A compound of formula (29) in which $R^3$ and $R^4$ together form a ring may be obtained by cyclizing a compound of formula (28), according to the reaction scheme mentioned below.

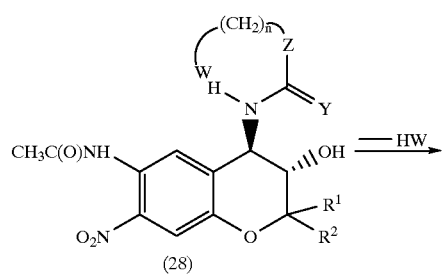

-continued

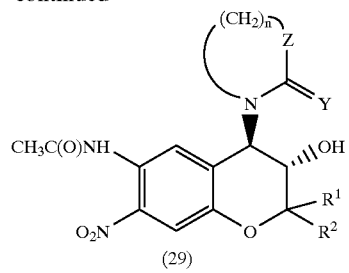

(29)

The solvent to be used for the reaction of the compound of formula (25) and the compound of Y=C=N—R⁶ or ClC(Y)OR⁶ includes, for example, sulfoxide solvents such as dimethylsulfoxide, amide solvents such as dimethylformamide or dimethylacetamide, ether solvents such as ethyl ether, dimethoxyethane or tetrahydrofuran, and halogenated compound solvents such as methylene chloride or chloroform. Of these, preferred are halogenated compound solvents.

The reaction temperature may be from the ice-cooled temperature to the heated reflux temperature, the reaction temperature of the reaction solvent, preferably at the reflux temperature for the solvent used. If desired, the reaction may be conducted under pressure.

Regarding the molar ratio of the starting compounds, the ratio of compound (25)/Y=C=N—R⁶ or ClC(Y)OR⁶ (by molar ratio) is within the range of from 0.5 to 2.0, preferably from 1.0 to 1.1.

Of the compounds of formula (I) of the present invention, those where A is an acyl group may be obtained by reacting a compound of formula (30) with an acylating agent in an inert solvent in the presence of a suitable base, according to the reaction scheme mentioned below.

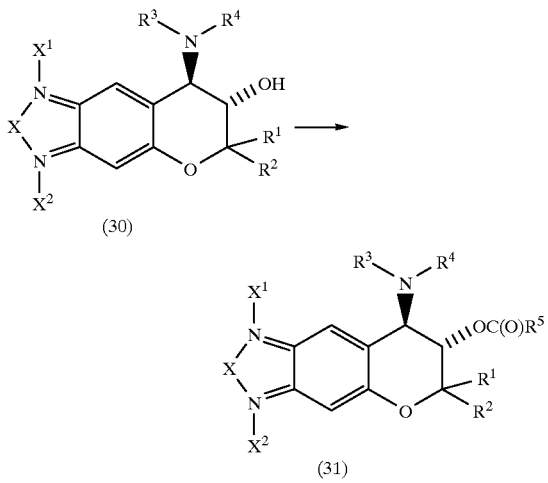

The solvent to be used for the reaction includes, for example, sulfoxide solvents such as dimethylsulfoxide, amide solvents such as dimethylformamide or dimethylacetamide, ether solvents such as ethyl ether, dimethoxyethane or tetrahydrofuran, and halogenated compound solvents such as dichloromethane, chloroform or dichloroethane. The reaction may be conducted in the absence of the solvent. The base to be used for the reaction includes, for example, triethylamine, pyridine, diisopropylethylamine and DBU (diazabicycloundecene). The acylating agent includes acid halides such as acid chlorides and acid bromides, and acid anhydrides. The reaction temperature compounds may be from an ice-cooled temperature to the reflux temperature for the reaction solvent used.

Regarding the molar ratio of the starting compounds, the ratio of the compound of (30) to the acylating agent is within the range of from 0.5 to 2.0, preferably from 1.0 to 1.1.

Of the compounds of formula (I) of the present invention, compounds in which $R^4$ is NC(N—CN)NHR⁹ may be obtained according to the reaction scheme mentioned below, in which a compound of formula (32) is reacted with carbodiimide in an inert solvent, then subjected to removing hydrogen sulfide and thereafter reacted with cyanamide to give a compound of formula (33). A compound of formula (34) in which $R^3$ and $R^4$ together form a cyclic thiourea may also be led to a compound of formula (35) by the same reaction process.

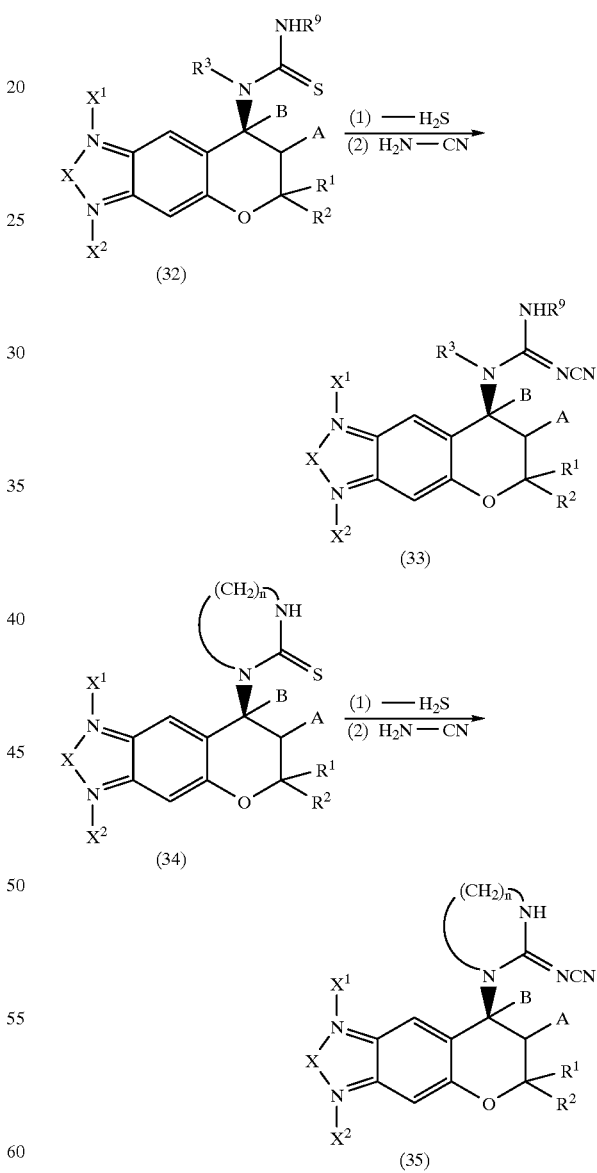

Of the compounds of formula (I) of the present invention, optically active isomers may be produced, for example, by methods of optical resolution of racemic modifications (see Japanese Patent Laid-Open Application No. 3-141286, U.S. Pat. No. 5,097,037, European Patent No. 409,165) and methods of asymmetric synthesis (see Japanese Patent Application Laid-Open No. 5-301878, European Patent No. 535,377).

As mentioned above, the present inventors have found that the compounds of formula (I) have a strong activity of reinforcing the contraction of cardiac muscles and also have a strong activity of reducing the rate of heart beats. Since the compounds of the present invention have no activity of retarding cardiac functions but rather have an activity of enhancing the contraction of cardiac muscles, they may exert the activity of reducing the rate of heart beats even when they are administered in the same amount as that necessary for expressing the cardiotonic activity. Because of their activities, it is considered that the compounds according to the present invention may reduce the amount of oxygen to be consumed by cardiac muscles to therefore reduce the motility load of cardiac muscles and exert the anti-stenocardiac activity. In addition, it is also considered that they have an activity of prolonging the effective refractory period to thereby exert an anti-arrhythmic activity. Therefore, it is expected that the compounds of the present invention are useful for curing cardiovascular disorders in consideration of the oxygen consumption, the energy consumption or the metabolism caused by the cardiac motility and also for curing other cardiac disorders essentially in consideration of the activity of the compounds of reducing the rate of heart beats. For example, the compounds of the present invention are useful as medicines for cardiac insufficiency of mammals including human beings and also as medicines for curing cardiovascular disorders causing cardiac insufficiency of them such as, for example, as medicines for curing ischemic cardiopathy, medicines for curing hypertension, medicines for curing cardiac fluid retention, medicines for curing pulmonary hypertension, medicines for curing valvulitis, medicines for curing congenital cardiac disorders, medicines for curing cardiomuscular disorders, medicines for curing pulmonary edema, medicines for curing angina of effort, medicines for curing myocardial infarction, medicines for curing arrhythmia, and medicines for curing atrial fibrillation.

The present invention provides pharmaceutical compositions containing an effective amount of the compounds of formula (I) for curing these diseases.

As the manner of administration of the compounds of the present invention, there may be mentioned parenterally administ- ration by injections (subcutaneous, intraveneous, intramuscular or intraperitoneal injection), ointments, suppositories or aerosols, or an oral administration in the form of tablets, capsules, granules, pills, syrups, liquids,. emulsions or suspensions.

The above pharmacological or veterinary compositions of the present invention contain the above-mentioned compounds of the present invention in an amount of from about 0.01 to 99.5% by weight, preferably from about 0.1 to 30% by weight, based on the total weight of the composition.

To the compounds of the present invention or to the compositions containing the present compounds, other pharmacologically or veterinarily active compounds may be incorporated. Further, the compositions of the present invention may contain a plurality of the compounds of the present invention.

The clinical dose of the compounds of the present invention varies depending upon the age, the body weight, the sensitivity or the symptom etc. of the patient. In general, however, the effective daily dose is usually from about 0.003 to 1.5 g, preferably from about 0.01 to 0.6 g for an adult. If necessary, however, an amount outside the above range may be employed.

The compounds of the invention may be prepared into various suitable formulations depending upon the manner of administration, in accordance with conventional methods commonly employed for the preparations of pharmaceutical formulations.

Namely, tablets, capsules, granules or pills for oral administration, may be prepared by using excipients such as white sugar, lactose, glucose, starch or mannitol; binders such as hydroxypropyl cellulose, syrups, arabic gum, gelatin, sorbitol, tragacanth gum, methyl cellulose or poly-vinylpyrrolidone; disintegrants such as starch, carboxymethyl cellulose or its calcium salt, crystal cellulose powder or polyethylene glycol; lubricants such as talc, magnesium or calcium stearate, silica; and smoothers such as sodium laurate, glycerol, etc.

The injections, solutions (liquids), emulsions, suspensions, syrups or aerosol may be prepared using a solvent for the active ingredient such as water, ethyl alcohol, isopropyl alcohol, propylene glycol, 1,3-butylene glycol or polyethylene glycol; surfactants such as sorbitan fatty acid esters, polyoxyethylene sorbitan fatty acid esters, polyoxyethylene fatty acid esters, polyoxyethylene ether of hydrogenated castor oil, lecithin; suspending agents such as cellulose derivatives such as sodium salt of carboxymethyl, cellulose derivatives such as methyl cellulose or natural rubbers such as tragacanth or arabic gum; or preservatives such as para-hydroxybenzoic acid, benzalkonium chloride, salts of sorbic acid, etc.

Ointments which are an endermic preparation may be be prepared by using, e.g., white vaseline, liquid paraffin, higher alcohols, Macrogol ointment, hydrophilic ointment base or hydrogel base, etc.

The suppositories may be prepared by using, e.g., cacao butter, polyethylene glycol, lanolin, fatty acid triglycerides, coconut oil, polysorbate, etc.

BEST MODE FOR CARRYING OUT THE INVENTION

Now the present invention is explained referring to examples, but it is not to be limited to these examples.

SYNTHESIS EXAMPLES

Synthesis examples of preparing the compounds which are usable as medicines of the present invention are given below.

Reference Example 1

Synthesis of Optically active 7,8-dihydro-6,6-dimethyl-7,8-epoxy-6H-pyrano[2,3-f]benzo-2,1,3-oxadiazole To 300 ml of a methylene chloride solution containing 40 g (198 mmol) of 6,6-dimethyl-6H-pyrano[2,3-f]benzo-2,1, 3-oxadiazole were added 2.44 g (3.7 mmol) of (R,R)-[1,2-bis[3,5-di-t-butyl-salicylidamino)cyclohexane]-manganese (III) acetate. (The production of the acetate is described in Japanese Patent Application Laid-Open No. Hei 5-507645 and European Patent No. 521,099.) The mixture was added with 1.2 liters of an aqueous solution of sodium hypochlorite (active chlorine content: 5%). While adjusting the pH of the reaction system at 11.3 with a pH-stat, aqueous solution of 0.5 N-sodium hydroxide was added thereto. The resulting solution was stirred at room temperature for 10 hours. After stopping the stirring, the solution was allowed to stand at room temperature overnight. The reaction solution was extracted with chloroform (300 ml×1; 200 ml×1; 50 ml×1)

and dried over anhydrous sodium sulfate, and the solvent was distilled off under reduced pressure. The residue was subjected to silica gel column chromatography (benzene:ethyl acetate=5:1) and again to silica gel column chromatography (benzene→benzene-ethyl acetate=5:1), and the crystals obtained were recrystallized from ethanol (60 ml) to obtain 15.7 g of the intended compound. (yield: 36%) optical purity >99% ee.

Column: Chiralcell OJ (of Daisel Chemical Industries, Ltd.)
Mobile Phase: Hexane:isopropanol=4:1
Detection: UV 254 nm
Flow Rate: One ml/min
Column Temperature: 40° C.
Retention Time: 9.2 min.

Reference Example 2

Synthesis of Enantiomer of Compound of Reference Example 1

An enantiomer of the compound of Reference Example 1 was synthesized in the same manner as in Reference Example 1, using (S,S)-[1,2-bis(3,5-di-t-butylsalicylidamino)cyclohexane]-manganese(III) acetate. The yield of the product was 20.8 g (48%).

Optical purity >99% ee
[retention time: 12.5 min].

Synthesis Example 1

Synthesis of 7,8-dihydro-6,6-dimethyl-7-hydroxy-8-diethylamino-6H-pyrano[2,3-f]benzo-2,1,3-oxadiazole-3-oxide

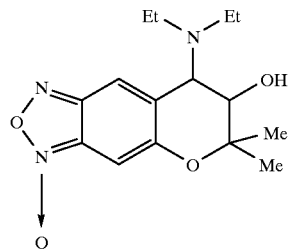

465 mg (1.50 mmol) of 3,4-dihydro-2,2-dimethyl-3-hydroxy-4-diethylamino-6-amino-7-nitro-2H-benzo[b]pyran, 102 mg (2.56 mmol) of sodium hydroxide, 32 ml of ethanol, 6 ml of water and 0.1 ml of polyethylene glycol were stirred at 40° C., and 2.59 g (2.10 mmol) of aqueous 6% NaOCl solution were added to the resulting solution and stirred for 15 minutes. The reaction liquid was poured into water and extracted thrice with ethyl acetate. The ethyl acetate layers were collected and then washed with water, then saturated saline solution, and dried over anhydrous sodium sulfate. The solvent was distilled off, and the residue was subjected to silica gel column chromatography (eluent: ethyl acetate-hexane=1:2 (v/v)) to obtain 189 mg of the intended compound. (yield: 41%) A part of the compound thus obtained was dissolved in ethanol, and HCl-EtOH solution and absolute ether were added thereto in order whereupon hydrochloride of the compound was obtained as yellow crystals. The salt had the following properties:

m.p.: 160 to 164° C. (decomposition)
NMR (CDCl$_3$)δ (ppm): 1.15(6H), 1.26(3H), 1.52(3H), 2.64–3.14(5H), 3,56(1H), 3.85(1H), 6.57(1H), 7.30(1H)

Synthesis Example 2

Synthesis of 7,8-dihydro-6,6-dimethyl-7-hydroxy-8-(1-piperidinyl)-6H-pyrano[2,3-f]benzo-2,1,3-oxadiazole-3-oxide

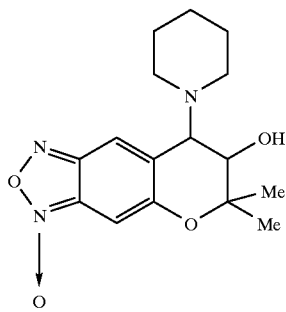

924 mg (2.88 mmol) of 3,4-dihydro-2,2-dimethyl-3-hydroxy-4-(1-piperidinyl)-6-amino-7-nitro-2H-benzo[b]pyran, 0.7 ml of 50% potassium hydroxide, 4 ml of dichloromethane and 10 mg of Bu$_4$N$^+$Br- were stirred at room temperature, and 4.97 g (4.03 mmol) of aqueous 6% NaOCl solution were added thereto and reacted for 9 hours while stirring at room temperature. The organic layer was separated, and the aqueous layer was extracted twice with methylene chloride. The methylene chloride layers were combined, washed with water and dried over anhydrous sodium sulfate, and the solvent was distilled off. The residue was subjected to silica gel column chromatography (eluent: ethyl acetate-hexane=1:3 (v/v)) to obtain 297 mg of the intended compound as oil. (yield: 43%) A part of the compound thus obtained was dissolved in ethanol and HCl-EtOH and dry ether were added thereto in order whereupon hydrochloride of the intended compound was obtained as yellow crystals.

m.p.: 210–213° C.

Synthesis Example 3

Synthesis of 7,8-dihydro-6,6-dimethyl-7-hydroxy-8-(1-piperidinyl)-6H-pyrano[2,3-f]benzo-2,1,3-oxadiazole

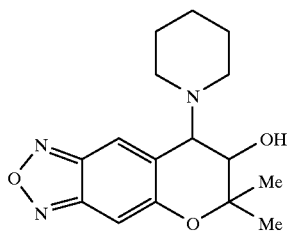

297 mg (0.93 mmol) of 7,8-dihydro-6,6-dimethyl-7-hydroxy-8-(1-piperidinyl)-6H-pyrano[2,3-f]benzo-2,1,3-oxadiazole-3-oxide obtained in Synthesis Example 2, 6 ml of ethylene glycol and 60 mg (0.93 mmol) of NaN$_3$ were heated at 140° C. and reacted for 1.2 hours. After cooled, the reaction liquid was poured into water and extracted thrice with chloroform. The chloroform layers were combined and dried over anhydrous sodium sulfate, and the solvent was then distilled off. The residue was subjected to column chromatography (eluent: ethyl acetate-hexane=1:3 (v/v)) to obtain 84 mg of the intended compound. (yield: 30%) A part of the compound thus obtained was dissolved in ethanol/ethyl ether and HCl-EtOH was added thereto whereupon hydrochloride of the compound was obtained as pale yellow crystals.

m.p.: 202 to 205° C.

Synthesis Example 4

Synthesis of 7,8-dihydro-6,6-dimethyl-7-hydroxy-8-(1-pyrrolidinyl)-6H-pyrano[2,3-f]benzo-2,1,3-oxadiazole

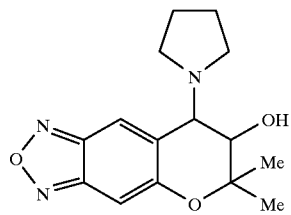

150 mg (0.687 mmol) of 7,8-dihydro-6,6-dimethyl-7,8-epoxy-6H-pyrano[2,3-f]benzo-2,1,3-oxadiazole, 63 μl (0.756 mmol) of pyrrolidine and 2 ml of ethanol were refluxed for 31 hours while stirring. The solvent was distilled off, and the residue was subjected to partitioning thin-layer chromatography (eluent: ethyl acetate-hexane=1:1 (v/v)) to obtain 120 mg of the intended compound. (yield: 60%) A part of the compound thus obtained was dissolved in dry ether and HCl-EtOH was added thereto whereupon hydrochloride of the compound was obtained as pale yellow crystals.

m.p.: 208 to 209° C.

Synthesis Example 5

Synthesis of 7,8-dihydro-6,6-dimethyl-7-hydroxy-8-methylamino-6H-pyrano[2,3-f]benzo-2,1,3-oxadiazole

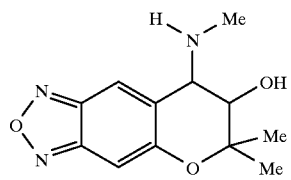

300 mg (1.37 mmol) of 7,8-dihydro-6,6-dimethyl-7,8-epoxy-6H-pyrano[2,3-f]benzo-2,1,3-oxadiazole, 0.53 g of aqueous 40% methylamine solution and 15 ml of ethanol were stirred at 60° C. for 3 days, using a pressure tube. After the reaction, the solvent was distilled off, and the residue was subjected to partitioning thin-layer chromatography (eluent: ethyl acetate-methanol=10:1) to obtain 263 mg of the intended compound. (yield: 77%) A part of the compound thus obtained was dissolved in dry ether and HCl-EtOH was added thereto whereupon hydrochloride of the compound was obtained as colorless crystals.

m.p.: 244.5 to 260° C.

Synthesis Example 6

Synthesis of 7,8-dihydro-6,6-dimethyl-7-hydroxy-8-(4-fluorobenzyl)amino-6H-pyrano[2,3-f]benzo-2,1,3-oxadiazole

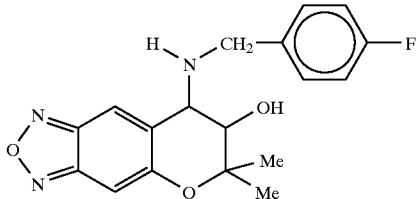

150 mg (0.687 mmol) of 7,8-dihydro-6,6-dimethyl-7,8-epoxy-6H-pyrano[2,3-f]benzo-2,1,3-oxadiazole, 86 μl (0.756 mmol) of 4-fluorobenzylamine and 2 ml of ethanol were refluxed for 20 hours while stirring. The solvent was distilled off, and the residue was subjected to partitioning thin-layer chromatography (eluent: ethyl acetate-hexane=1:2) to obtain 204 mg of the intended compound as an oil. (yield: 86%) A part of the compound thus obtained was dissolved in dry ether and HCl-EtOH was added thereto whereupon hydrochloride of the compound was obtained as colorless crystals.

m.p.: 207 to 210° C.

Synthesis Example 7

Synthesis of 7,8-dihydro-6,6-dimethyl-7-hydroxy-8-benzylamino-6H-pyrano[2,3-f]benzo-2,1,3-oxadiazole

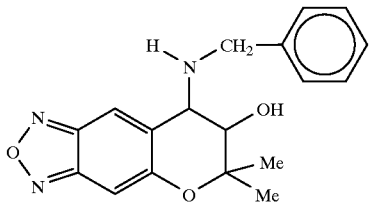

Using benzylamine, the intended compound was obtained in the same manner as in Synthesis Example 6.

NMR(60 MHz, CDCl$_3$, δ ppm): 7.77(1H), 7.37–6.92(5H), 6.81(1H), 3.9–3.8(4H), 2.73(2H), 1.51(3H), 1.25(3H)

Synthesis Example 8

Synthesis of 7,8-dihydro-6,6-dimethyl-7-hydroxy-8-(N-benzyl-N-methyl)amino-6H-pyrano[2,3-f]benzo-2,1,3-oxadiazole

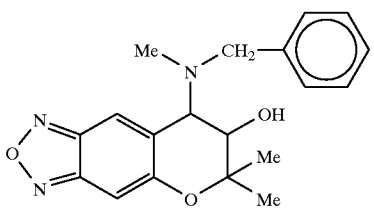

Using N-methylbenzylamine, the intended compound was obtained in the same manner as in Synthesis Example 6. Hydrochloride of the intended compound had a melting point of 148 to 150° C.

Synthesis Example 9

Synthesis of 7,8-dihydro-6,6-dimethyl-7-hydroxy-8-cyclohexylamino-6H-pyrano[2,3-f]benzo-2,1,3-oxadiazole:

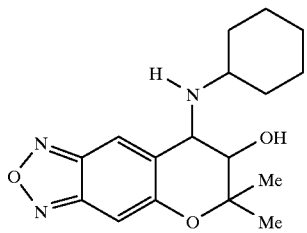

Using cyclohexylamine, the intended compound was obtained in the same manner as in Synthesis Example 6. Hydrochloride of the intended compound had a melting point of 208 to 210° C.

Synthesis Example 10

Synthesis of 7,8-dihydro-6,6-dimethyl-7-hydroxy-8-(4-methyl-1-piperazinyl)-6H-pyrano[2,3-f]benzo-2,1,3-oxadiazole

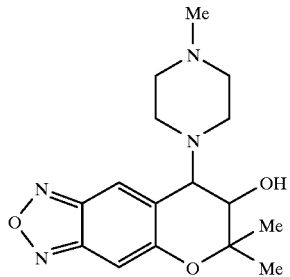

Using N-methylpiperazine, the intended compound was obtained as yellow crystals in the same manner as in Synthesis Example 6. (yield: 75%)

m.p.: 225 to 226° C.

MS: 70(100%), 246(56%), 318($M^+$, 13%)

Synthesis Example 11

Synthesis of 7,8-dihydro-6,6-dimethyl-7-hydroxy-8-(1-piperazinyl)-6H-pyrano[2,3-f]benzo-2,1,3-oxadiazole

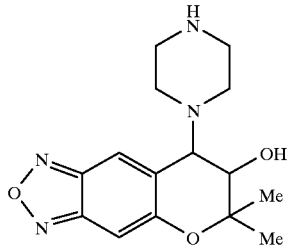

Using piperazine, the intended compound was obtained as pale yellow crystals in the same manner as in Synthesis Example 6. (yield: 72%)

m.p.: 245 to 246° C.

MS: 56(67%), 232(100%), 304($M^+$, 8%)

Synthesis Example 12

Synthesis of 7,8-dihydro-6,6-dimethyl-7-hydroxy-8-(4-phenyl-1-piperazinyl)-6H-pyrano[2,3-f]benzo-2,1,3-oxadiazole

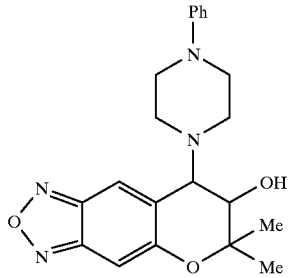

Using N-phenylpiperazine, the intended compound was obtained in the same manner as in Synthesis Example 6. (yield: 75%)

MS: 132(100%), 308(36%), 380($M^+$, 32%)

Hydrochloride of the compound was obtained as colorless crystals.

m.p.: 198 to 201° C.

Synthesis Example 13

Synthesis of 7,8-dihydro-6,6-dimethyl-7-hydroxy-8-(4-phenyl-1-piperidinyl)-6H-pyrano[2,3-f]benzo-2,1,3-oxadiazole

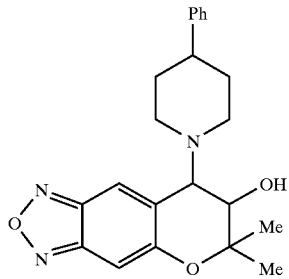

Using 4-phenylpiperidine, the intended compound was obtained in the same manner as in Synthesis Example 6. (yield: 87%)

MS: 186(21%), 307(100%), 379(M$^+$, 4%)

Hydrochloride of the compound was obtained as colorless crystals.

m.p.: 195 to 197° C.

Synthesis Example 14

Synthesis of 7,8-dihydro-6,6-dimethyl-7-hydroxy-8-(1,2,3,4-tetrahydroisoquinolin-2-yl)-6H-pyrano[2,3-f]benzo-2,1,3-oxadiazole

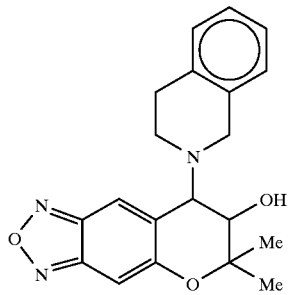

Using 1,2,3,4-tetrahydroisoquinoline, the intended compound was obtained in the same manner as in Synthesis Example 6. (yield: 80%)

MS: 262(32%), 279(100%), 351(M$^+$, 4%) Hydrochloride of the compound was obtained as colorless crystals.

m.p.: 188.5 to 190° C.

Synthesis Example 15

Synthesis of 7,8-dihydro-6,6-dimethyl-7-hydroxy-8-(4-morpholinyl)-6H-pyrano[2,3-f]benzo-2,1,3-oxadiazole

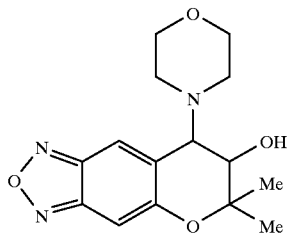

Using morpholine, the intended compound was obtained in the same manner as in Synthesis Example 6. (yield: 11%)

m.p.: 185 to 186.5° C.

Synthesis Example 16

Synthesis of 7,8-dihydro-6,6-dimethyl-7-hydroxy-8-(3-methoxypropylamino)-6H-pyrano[2,3-f]benzo-2,1,3-oxadiazole

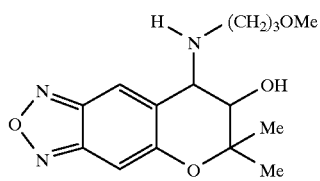

Using 3-methoxypropylamine, the intended compound was obtained in the same manner as in Synthesis Example 6. (yield: 60%)

MS: 177(100%), 235(100%), 289(M$^+$–18, 1%)

m.p.: 175.5 to 178° C.

Synthesis Example 17

Synthesis of 7,8-dihydro-6,6-dimethyl-7-hydroxy-8-(3-ethoxycarbonylpropylamino)-6H-pyrano[2,3-f]benzo-2,1,3-oxadiazole

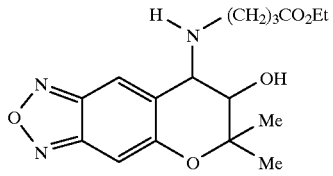

Using ethyl 4-aminobutyrate, the intended compound was obtained in the same manner as in Synthesis Example 6. (yield: 38%)

Hydrochloride of the compound was obtained as colorless crystals.

m.p.: 189 to 191° C.

Synthesis Example 18

Synthesis of 7,8-dihydro-6,6-dimethyl-7-hydroxy-8-ethoxycarbonylmethylamino-6H-pyrano[2,3-f]benzo-2,1,3-oxadiazole

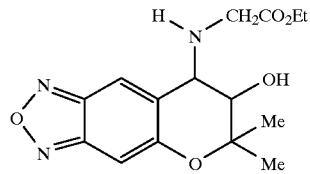

Using glycine ethyl ester, the intended compound was obtained in the same manner as in Synthesis Example 6. (yield: 5%)

Hydrochloride of the compound was obtained as an orange oil.

Synthesis Example 19

Synthesis of 7,8-dihydro-6,6-dimethyl-7-hydroxy-8-(3-chloropropylamino)-6H-pyrano[2,3-f]benzo-2,1,3-oxadiazole

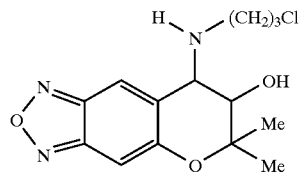

Using 3-chloropropylamine, the intended compound was obtained in the same manner as in Synthesis Example 6. (yield: 20%)

Hydrochloride of the compound was obtained as colorless crystals.

m.p.: 216 to 220° C.

Synthesis Example 20

Synthesis of 7,8-dihydro-6,6-dimethyl-7-hydroxy-8-(2-hydroxyethylamino)-6H-pyrano[2,3-f]benzo-2,1,3-oxadiazole

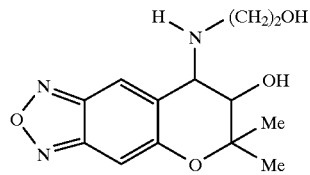

Using ethanolamine, the intended compound was obtained in the same manner as in Synthesis Example 6. (yield: 89%)

Hydrochloride of the compound was obtained as colorless crystals.

m.p.: 200 to 204° C.

Synthesis Example 21

Synthesis of 7,8-dihydro-6,6-dimethyl-7-hydroxy-8-amino-6H-pyrano[2,3-f]benzo-2,1,3-oxadiazole

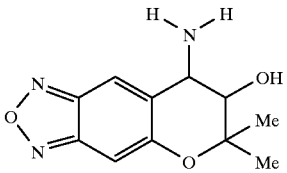

0.82 g (3.8 mmol) of 7,8-dihydro-6,6-dimethyl-7,8-epoxy-6H-pyrano[2,3-f]benzo-2,1,3-oxadiazole were dissolved in 25 ml of 16.7% $NH_3$-EtOH and reacted for at 60° C. for 48 hours in a pressure glass tube. The solvent was distilled off, and the residue was subjected to silica gel column chromatography (eluent: ethyl acetate-methanol= 5:1) to obtain 0.77 g of the intended compound as a brown solid. (yield: 87%) A part of the product was recrystallized from ethanol to obtain pure colorless crystals of the intended compound.

m.p.: 223 to 225° C.

NMR($CDCl_3$+DMSO-$d^6$) δ (ppm): 1.26(3H), 1.49(3H), 2.80–3.30(5H), 3.33(1H), 3.78(1H), 6.82(1H), 7.98(1H),

MS: 133(50%), 163(100%), 235($M^+$, 3%)

Synthesis Example 22

Synthesis of 7,8-dihydro-6,6-dimetyl-7-hydroxy-8-methylureido-6H-pyrano[2,3-f]benzo-2,1,3-oxadiazole

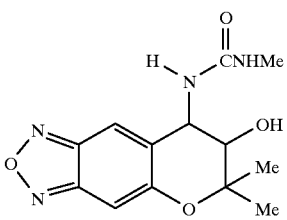

200 mg (0.850 mmol) of 7,8-dihydro-6,6-dimethyl-7-hydroxy-8-amino-6H-pyrano[2,3-f]benzo-2,1,3-oxadiazole and 20 ml of dichloromethane were stirred at room temperature, and 55 μl (0.935 mmol) of methyl isocyanate were added thereto and stirred for 23 hours. The crystals precipitated were filtered to obtain 227 mg of the intended compound as colorless crystals. (yield: 92%)

m.p.: 213 to 215° C.

MS: 44, 202(30%), 274($M^+$—$H_2O$, 6%)

Synthesis Example 23

Synthesis of 7,8-dihydro-6,6-dimethyl-7-hydroxy-8-methylthioureido-6H-pyrano[2,3-f]benzo-2,1,3-oxadiazole

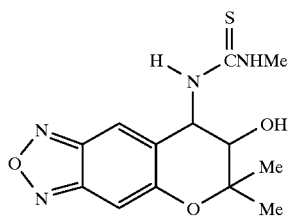

200 mg (0.850 mmol) of 7,8-dihydro-6,6-dimethyl-7-hydroxy-8-amino-6H-pyrano[2,3-f]benzo-2,1,3-oxadiazole and 20 ml of dichloromethane were stirred at room temperature, and 68 mg (0.935 mmol) of methyl isothiocyanate were added thereto and stirred for 23 hours. The crystals precipitated were filtered off to obtain 122 mg of the intended compound as colorless crystals. (yield: 47%)

m.p.: 213 to 215° C.

MS: 91(62%), 202(67%), 290, 308(M$^+$, 27%)

Synthesis Example 24

Synthesis of 7,8-dihydro-6,6-dimethyl-7-hydroxy-8-phenylureido-6H-pyrano[2,3-f]benzo-2,1,3-oxadiazole

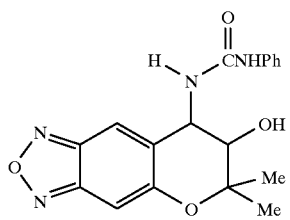

200 mg (0.850 mmol) of 7,8-dihydro-6,6-dimethyl-7-hydroxy-8-amino-6H-pyrano[2,3-f]benzo-2,1,3-oxadiazole and 20 ml of dichloromethane were stirred at room temperature, and 102 μl (0.935 mmol) of phenyl isocyanate were added thereto and stirred for 4 hours. The crystals precipitated were filtered off to obtain 203 mg of the intended compound as colorless crystals. (yield: 67%)

m.p. : 215 to 217° C.

MS: 93, 163(56%), 321(20%), 354(M$^+$, 10%)

Synthesis Example 25

Synthesis of 7,8-dihydro-6,6-dimethyl-7-hydroxy-8-trichloroacetylureido-6H-pyrano[2,3-f]benzo-2,1,3-oxadiazole

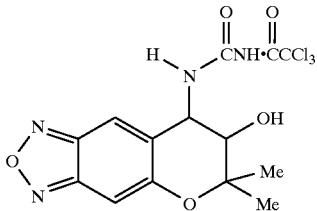

200 mg (0.850 mmol) of 7,8-dihydro-6,6-dimethyl-7-hydroxy-8-amino-6H-pyrano[2,3-f]benzo-2,1,3-oxadiazole and 20 ml of dichloromethane were stirred at room temperature, and 100 μl (0.935 mmol) of trichloroacetyl isocyanate were added thereto and stirred for 5 hours. The crystals precipitated were filtered off to obtain 90 mg of the intended compoundas colorless crystals. (yield: 25%)

m.p.: 248 to 250° C.

MS: 44, 163(43%), 422(M$^+$, 2%)

Synthesis Example 26

Synthesis of 7,8-dihydro-6,6-dimethyl-7-hydroxy-8-(3-chloropropylureido)-6H-pyrano[2,3-f]benzo-2,1,3-oxadiazole

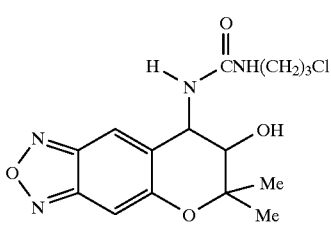

400 mg (1.70 mmol) of 7,8-dihydro-6,6-dimethyl-7-hydroxy-8-amino-6H-pyrano[2,3-f]benzo-2,1,3-oxadiazole and 40 ml of dichloromethane were stirred at room temperature, and 192 μl (1.87 mmol) of 3-chloropropyl isocyanate were added thereto and stirred for 5 hours. The crystals precipitated were taken out by filtration to obtain 250 mg of the intended compound as pale yellow crystals. (yield: 41%)

m.p.: 83 to 85° C.

MS: 41(53%), 163, 318(93%), 354(M$^+$, 5%)

Synthesis Example 27

Synthesis of 7,8-dihydro-6,6-dimethyl-7-hydroxy-8-(2-chloroethylureido)-6H-pyrano[2,3-f]benzo-2,1,3-oxadiazole

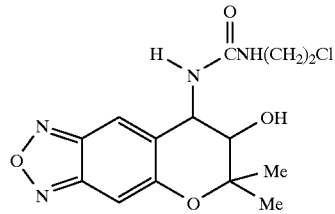

400 mg (1.70 mmol) of 7,8-dihydro-6,6-dimethyl-7-hydroxy-8-amino-6H-pyrano[2,3-f]benzo-2,1,3-oxadiazole and 40 ml of dichloromethane were stirred at room temperature, and 200 µl (1.87 mmol) of 2-chloroethyl isocyanate were added thereto and stirred for 6 hours. The crystals precipitated were filtered off to obtain 480 mg of the intended compound as colorless crystals. (yield: 83%).

m.p.: 178 to 180° C.

MS: 87(57%), 163, 304(78%), 340(M$^+$, 8%)

Synthesis Example 28

Synthesis of 7,8-dihydro-6,6-dimethyl-7-hydroxy-8-isopropylureido-6H-pyrano[2,3-f]benzo-2,1,3-oxadiazole

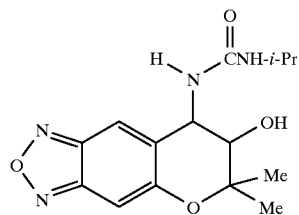

200 mg (0.850 mmol) of 7,8-dihydro-6,6-dimethyl-7-hydroxy-8-amino-6H-pyrano[2,3-f]benzo-2,1,3-oxadiazole and 20 ml of dichloromethane were stirred at room temperature, and 92 µl (0.935 mmol) of isopropyl isocyanate were added thereto and stirred for 6 hours. The crystals precipitated were filtered off to obtain 120 mg of the intended compound as colorless crystals. (yield: 44%)

m.p.: 201 to 203° C.

MS: 43(40%), 202, 302(20%), 320(M$^+$, 12%)

Synthesis Example 29

Synthesis of 7,8-dihydro-6,6-dimethyl-7-hydroxy-8-ethoxycarbonylamino-6H-pyrano[2,3-f]benzo-2,1,3-oxadiazole

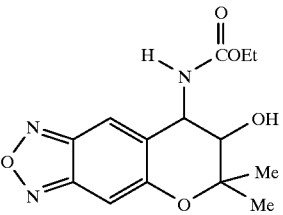

200 mg (0.850 mmol) of 7,8-dihydro-6,6-dimethyl-7-hydroxy-8-amino-6H-pyrano[2,3-f]benzo-2,1,3-oxadiazole, 166 µl (1.19 mmol) of triethylamine and 20 mg of dichloromethane were stirred at room temperature, and 114 µl (1.19 mmol) of ethyl chloroformate were added thereto and stirred for 21 hours. The reaction liquid was washed thrice with water and then dried over anhydrous sodium sulfate. The solvent was distilled off, and the residue was subjected to silica gel column chromatography (eluent: ethyl acetate-methanol=20:1 (v/v)) to obtain 227 mg of the intended compound as an yellow oil. (yield: 87%)

MS: 133(48%), 235, 307(M$^+$, 25%)

Synthesis Example 30

SYNTHESIS of 7,8-dihydro-6,6-dimethyl-7-hydroxy-8-(2-chloroethoxycarbonylamino)-6H-pyrano[2,3-f]benzo-2,1,3-oxadiazole

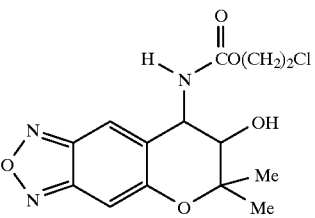

400 mg (1.70 mmol) of 7,8-dihydro-6,6-dimethyl-7-hydroxy-8-amino-6H-pyrano[2,3-f]benzo-2,1,3-oxadiazole, 260 µl (1.87 mmol) of triethylamine and 40 mg of dichloromethane were stirred at room temperature, and 193 µl (1.87 mmol) of 2-chloroethyl chloroformate were added thereto and stirred for 21 hours. The reaction liquid was washed thrice with water and then dried over anhydrous sodium sulfate. The solvent was distilled off, and the residue was recrystallized from chloroform to obtain 507 mg of the intended compound as pale yellow crystals. (yield: 87%)

m.p.: 164 to 166° C.

MS: 133(48%), 235, 307(M$^+$, 25%)

Synthesis Example 31

Synthesis of 7,8-dihydro-6,6-dimethyl-7-hydroxy-8-(2-oxo-3-oxazolin-1-yl)-6H-pyrano[2,3-f]benzo-2,1,3-oxadiazole:

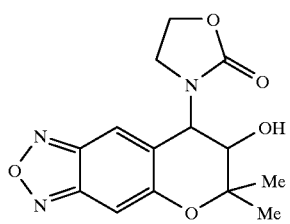

400 mg (1.17 mmol) of the compound obtained in Synthesis Example 30, 3.24 g (23.4 mmol) of potassium carbonate, 388 mg (2.34 mmol) of potassium iodide and 50 ml of absolute acetone were heated under reflux at room temperature for 26 hours. After the mixture was cooled to room temperature, the insoluble matters were flitered off, ethyl acetate was added to the resulting filtrate, washed thrice with water. The compound thus obtained was dried over anhydrous magnesium sulfate, and the solvent was distilled off, and the residue was subjected to silica gel column chromatography (eluent: ethyl acetate-methanol= 10:1 (v/v)) to obtain 339 mg of the intended compound as a brown oil. (yield: 94%) A part of the product was recrystallized from ethyl acetate to obtain yellow crystals having the following physical data:

m.p.: 177.5 to 180° C.

MS: 43(25%), 272, 287(65%), 305(M$^+$, 8%)

Synthesis Example 32

Synthesis of 7,8-dihydro-6,6-dimethyl-7-hydroxy-8-(2-oxo-3-imidazolin-1-yl)-6H-pyrano[2,3-f]benzo-2,1,3-oxadiazole

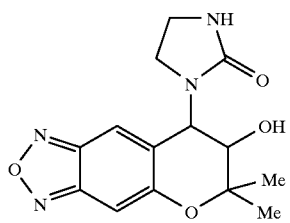

The compound obtained in Synthesis Example 27 was processed in the same manner as in Synthesis Example 31 to obtain the intended compound as colorless crystals. (yield: 34%)

m.p.: 251 to 252.5° C.

Synthesis Example 33

Synthesis of 7,8-dihydro-6,6-dimethyl-7-hydroxy-8-cyclohexylureido-6H-pyrano[2,3-f]benzo-2,1,3-oxadiazole

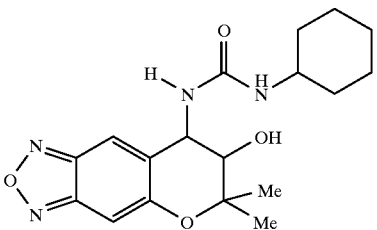

Using cyclohexyl isocyanate, the intended compound was obtained as colorless crystals in the same manner as in Synthesis Example 22. (yield: 28%)

m.p.: 203 to 206° C.

Synthesis Example 34

Synthesis of 7,8-dihydro-6,6-dimethyl-7-hydroxy-8-(t-butylureido)-6H-pyrano[2,3-f]benzo-2,1,3-oxadiazole

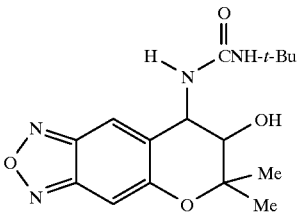

Using t-butyl isocyanate, the intended compound was obtained as colorless crystals in the same manner as in Synthesis Example 22. (yield: 52%)

m.p.: 203 to 205° C.

Synthesis Example 35

Synthesis of 7,8-dihydro-6,6-dimethyl-7-hydroxy-8-methoxycarbonylamino-6H-pyrano[2,3-f]benzo-2,1,3-oxadiazole

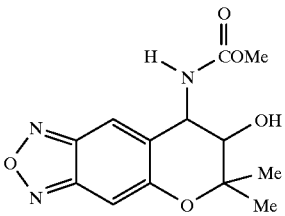

Using methyl chloroformate, the intended compound was obtained as a yellow oil in the same manner as in Synthesis Example 29. (yield: 19%)

Synthesis Example 36

Synthesis of 7,8-dihydro-6,6-dimethyl-7-hydroxy-8-(t-butylthioureido)-6H-pyrano[2,3-f]benzo-2,1,3-oxadiazole

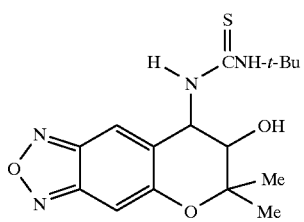

Using t-butyl isothiocyanate, the intended compound was obtained in the same manner as in Synthesis Example 23. (yield: 57%)

Synthesis Example 37

Synthesis of 7,8-dihydro-6,6-dimethyl-7-hydroxy-8-(2-oxohexahydropyrimidin-1-yl)-6H-pyrano[2,3-f]benzo-2,1,3-oxadiazole

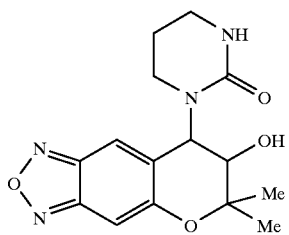

The compound obtained in Synthesis Example 26 was processed in the same manner as in Synthesis Example 31 to obtain the intended compound as colorless crystals. (yield: 39%)

m.p.: 233 to 234° C.

Synthesis Example 38

Synthesis of 7,8-dihydro-6,6-dimethyl-7-hydroxy-8-(3-chloropropoxycarbonylamino)-6H-pyrano[2,3-f]benzo-2,1,3-oxadiazole

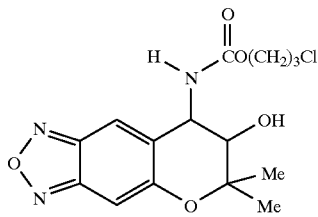

Using 3-chloropropyl chloroformate, the intended compound was obtained as an yellow oil in the same manner as in Synthesis Example 30. (yield: 100%)

Synthesis Example 39

Synthesis of 7,8-dihydro-6,6-dimethyl-7-hydroxy-8-(2-oxotetrahydroxazin-3-yl)-6H-pyrano[2,3-f]benzo-2,1,3-oxadiazole

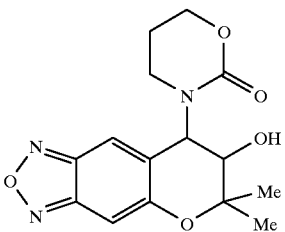

The compound obtained in Synthesis Example 38 was processed in the same manner as in Synthesis Example 31 to obtain the intended compound as colorless crystals. (yield: 34%)

m.p.: 220 to 234° C.

Synthesis Example 40

Synthesis of 7,8-dihydro-6,6-dimethyl-7-acetoxy-8-diethylamino-6H-pyrano[2,3-f]benzo-2,1,3-oxadiazole-3-oxide

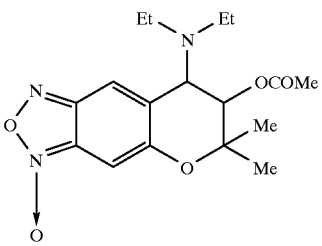

One ml of pyridine and 130 mg (1.27 mmol) of acetic anhydride were added to 103 mg (0.34 mmol) of the compound obtained in Synthesis Example 1 and stirred at 80 to 90° C. for 2 hours. After cooled, the solvent was distilled off under reduced pressure, and the residue was subjected to silicagel column chromatography (eluent: ethyl acetate-n-hexane=1:3 (v/v); Rf=0.3) to obtain 90.4 mg of the intended compound as an yellow solid. (yield: 77%)

Synthesis Example 41

Synthesis of 7,8-dihydro-6,6-dimethyl-7-hydroxy-8-diethylamino-6H-pyrano[2,3-f]benzo-2,1,3-oxadiazole

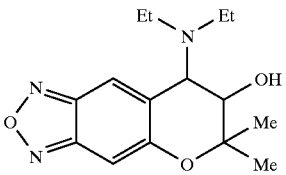

310 mg (1.01 mmol) of the compound obtained in Synthesis Example 1 were dissolved in 3 g of benzene, and 0.20 g (1.2 mmol) of triethyl phosphite were added thereto and heated at 60° C. for one hour. After cooled to room temperature, the compound thus obtained was stirred overnight. The solvent was distilled off under reduced pressure, and the residue was subjected to silicagel column chromatography (eluent: ethyl acetate-n-hexane=1:3 (v/v); Rf=0.3) to obtain 267 mg of the intended compound as an yellow solid. (yield: 91%)

Synthesis Example 42

Synthesis of 7,8-dihydro-6,6-dimethyl-7-acetoxy-8-diethylamino-6H-pyrano[2,3-f]benzo-2,1,3-oxadiazole

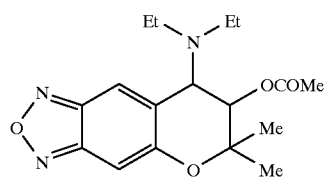

2 ml of pyridine and 0.29 g (2.8 mmol) of acetic anhydride were added to 220 mg (0.75 mmol) of the compound obtained in Synthesis Example 41 and heated at 80 to 90° C. for 2 hours. After cooled, the solvent was distilled off under reduced pressure, and the residue was subjected to silica gel column chromatography (eluent: ethyl acetate-n-hexane= 1:3 (v/v); Rf=0.3) to obtain 209.1 mg of the intended compound as a pale yellow solid. (yield: 83%)

Synthesis Example 43

Synthesis of 7,8-dihydro-6,6-dimethyl-7-acetoxy-8-(1-piperidinyl)-6H-pyrano[2,3-f]benzo-2,1,3-oxadiazole

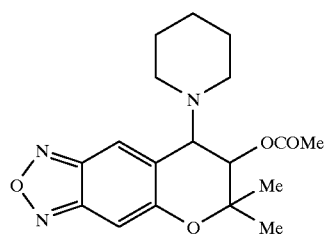

The compound obtained in Synthesis Example 3 was processed in the same manner as in Synthesis Example 42 to obtain the intended compound as yellow crystals. (yield: 100%)

m.p.: 158 to 160° C.

Synthesis Example 44

Synthesis of 7,8-dihydro-6,6-dimethyl-7-hydroxy-8-(4-diethoxybutylamino)-6H-pyrano[2,3-f]benzo-2,1,3-oxadiazole

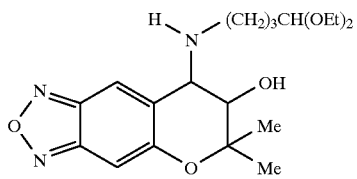

Using 4-aminobutylaldehyde diethylacetal, the intended compound was obtained as a brown oil in the same manner as in Synthesis Example 6. (yield: 93%)

Synthesis Example 45

Synthesis of 7,8-dihydro-6,6-dimethyl-7-hydroxy-8-(2-hydroxypyrrolidin-1-yl)-6H-pyrano[2,3-f]benzo-2,1,3-oxadiazole

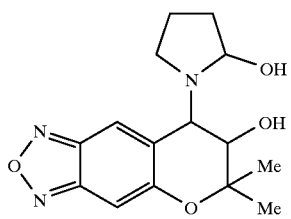

One ml of 2.5N hydrochloric acid and 2 ml of 1,4-dioxane were added to 316 mg (0.832 mmol) of the compound obtained in Synthesis Example 44 and reacted at room temperature for 3 hours. An aqueous sodium carbonate solution was added thereto so as to hydrate the product, and the resulting hydrate was then extracted with diethyl ether. The ether solution was dried with anhydrous sodium sulfate, and the solvent was distilled off under reduced pressure. The residue was subjected to silica gel column chromatography (eluent: ethyl acetate-n-hexane=1:1 (v/v); Rf=0.5) to obtain the intended compound as an yellow oil. (yield: 40%)

Synthesis Example 46

Synthesis of 7,8-dihydro-6,6-dimethyl-7-hydroxy-8-(3-carboxypropylamino)-6H-pyrano[2,3-f]benzo-2,1,3-oxadiazole

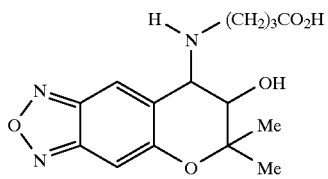

A solution of 18.4 mg (0.460 mmol) of sodium hydroxide, 1 ml of water and 4 ml of ethanol was added to 80.6 mg (0.209 mmol) of the hydrochloride obtained in Synthesis Example 17 and reacted for 3 hours at room temperature. The reaction mixture was made acidic by adding 1N hydrochloric acid thereto, and then extracted with diethyl ether.

This was dried over anhydrous sodium sulfate, and the solvent was distilled off under reduced pressure to obtain the intended compound as a colorless oil.

Synthesis Example 47

Synthesis of 7,8-dihydro-6,6-dimethyl-7-acetoxy-8-amino-6H-pyrano[2,3-f]benzo-2,1,3-oxadiazole

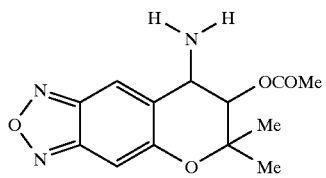

240 mg (1.10 mmol) of 7,8-dihydro-6,6-dimethyl-7,8-epoxy-6H-pyramo[2,3-f]benzo-2,1,3-oxadiazole were dissolved in 5 ml of dichloromethane, and 5 ml of acetonitrile and 0.5 ml of $BF_3$-diethyl ether complex were added thereto. After these were reacted at room temperature for 30 minutes, a saturated aqueous sodium hydrogencarbonate solution was added thereto and the reaction liquid was extracted with chloroform. After the extract was dried over anhydrous sodium sulfate, the solvent was distilled off under reduced pressure. The residue was subjected to silica gel column chromatography (eluent: ethyl acetate-n-hexane=1:1 (v/v); Rf=0.3) to obtain 152 mg of the intended compound as an yellow oil. (yield: 50%)

MS: 163(53%), 188(100%), 277($M^+$, 4%)

Synthesis Example 48

Synthesis of 7,8-dihydro-6,6-diethyl-7-hydroxy-8-(1-piperidinyl)-6H-pyrano[2,3-f]benzo-2,1,3-oxadiazole

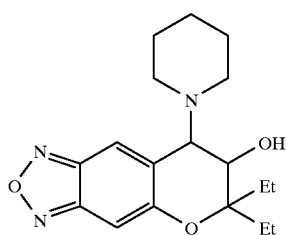

87.7 g (0.36 mmol) of 7,8-dihydro-6,6-diethyl-7,8-epoxy-6H-pyramo[2,3-f]benzo-2,1,3-oxadiazole, 61 mg (0.72 mmol) of piperidine and 2 ml of ethanol were refluxed for 20 hours while stirring. After the solvent was distilled off, the residue was subjected to silica gel column chromatography (eluent: ethyl acetate-n-hexane=1:1 (v/v); Rf=0.3) to obtain 30 mg of the intended compound as an yellow oil. (yield: 25%)

Synthesis Example 49

Synthesis of 7,8-dihydro-6,6-diethyl-7-hydroxy-8-amino-6H-pyrano[2,3-f]benzo-2,1,3-oxadiazole

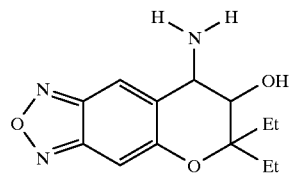

Using 7,8-dihydro-6,6-diethyl-7,8-epoxy-6H-pyrano[2,3-f]benzo-2,1,3-oxadiazole, the intended compound was obtained as colorless crystals in the same manner as in Synthesis Example 21. (yield: 44%)

m.p.: 122 to 124° C.

Synthesis Example 50

Synthesis of 7,8-dihydro-6,6-diethyl-7-hydroxy-8-methylureido-6H-pyrano[2,3-f]benzo-2,1,3-oxadiazole

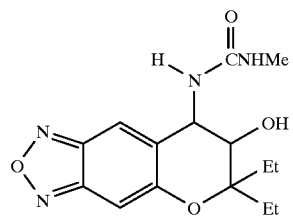

The compound obtained in Synthesis Example 49 was processed in the same manner as in Synthesis Example 22 to obtain the intended compound as a brown oil. (yield: 89%)

Synthesis Example 51

Synthesis of 7,8-dihydro-6,6-diethyl-7-acetoxy-8-amino-6H-pyrano[2,3-f]benzo-2,1,3-oxadiazole

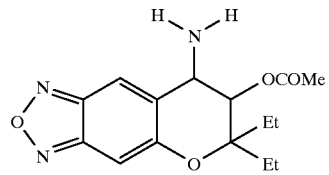

Using 7,8-dihydro-6,6-diethyl-7,8-epoxy-6H-pyrano[2,3-f]benzo-2,1,3-oxadiazole, the intended compound was obtained as pale yellow crystals in the same manner as in Synthesis Example 47. (yield: 62%)

m.p.: 92 to 95° C.

Synthesis Example 52

Synthesis of 7,8-dihydro-6,6-dimethyl-7-hydroxy-8-(2-cyano-3-t-butyl-1-guanidino)-6H-pyrano[2,3-f]benzo-2,1,3-oxadiazole

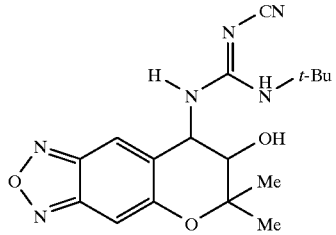

A solution comprised of 100 mg (0.29 mmol) of the compound obtained in Synthesis Example 36, 97 mg (0.37 mmol) of triphenylphosphine, 40 μl of carbon tetrachloride, 40 μl (0.29 mmol) of triethylamine and 1 ml of dichloromethane was heated under reflux for 4 hours. The solvent was removed by by distillation under reduced pressure, and the residue was subjected to silica gel column chromatography (eluent: ethyl acetate-n-hexane=1:2 (v/v); Rf=0.1) to obtain 77 mg of pale yellow crystals.

A solution comprised of 122 mg (0.39 mmol) of the compound thus obtained, 21 mg (0.50 mmol) of cyanamide, 2 ml of of tetrahydrofuran and 20 mg of diisopropylethylamine was stirred for 14 hours at room temperature. The crystals precipitated were taken out by filtration to obtain 112 mg of the intended compound as pale yellow crystals. (yield: 80%)

m.p.: 146 to 148° C.

Synthesis Example 53

Synthesis of 7,8-dihydro-6,6-dimethyl-7-hydroxy-8-(1-piperidinyl)-6H-pyrano[2,3-f]benzo-1,2,3-triazole

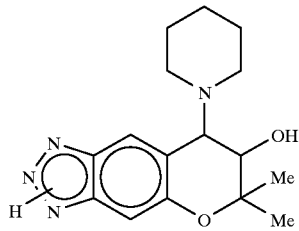

0.14 g (0.44 mmol) of 3,4-dihydro-2,2-dimethyl-3-hydroxy-4-(1-piperidinyl)-6-amino-7-nitro-2H-benzo[b]pyran were dissolved in 23.7 g of ethanol and hydroge gas was blown in the presence of 0.10 g of 5% palladiumcarbon, as a catalyst, for 3 hours at room temperature under one atmospheric pressure while stirring. The reaction liquid was filtered under suction to remove the catalyst therefrom, and the solvent was distilled off to obtain 0.12 g (yield: 95%) of 3,4-dihydro-2,2-dimethyl-3-hydroxy-4-(1-piperidinyl)-6-,7-diamino-2H-benzo[b]pyran as a dark red oil. As being unstable, this oil was directly used in the next diazotization.

The whole amount of the diamino compound obtained in the previous step was dissolved in a mixture of 0.13 g of acetic acid and 0.23 g of water, and a solution prepared by dissolving 35 mg (0.51 mmol) of sodium nitrite in 0.15 g of water was added thereto all at a time at room temperature. After the generation of heat was recognized, thus obtained compound was heated on a water bath at 80° C. for one minute. 20 ml of water, 0.13 g of sodium hydroxide and 4.0 g of sodium chloride were added to the reaction mixture, which was then extracted three times each with 40 ml of ethyl acetate. The ethyl acetate layers were combined, dried over anhydrous sodium sulfate and filtered. The solvent was distilled off to obtain 0.10 g of an yellowish red powder. 90 mg of the powder was purified by silica gel column chromatography (ethyl acetate-ethanol=5:1) to obtain 80 mg of the intended compound as a pale yellowish brown powder. The total yield through the two steps was 72%.

MS: 284(M$^+$-H$_2$O, 18%), 230(M$^+$-72, 100%), 84(5%)

Synthesis Example 54

Synthesis of 7,8-dihydro-6,6-dimethyl-7-hydroxy-8-(1-pyrrolidinyl)-6H-pyrano[2,3-f]benzo-1,2,3-triazole

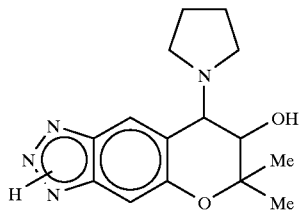

0.20 g (0.65 mmol) of 3,4-dihydro-2,2-dimethyl-3-hydroxy-4-(1-pyrrolidinyl)-6-amino-7-nitro-2H-benzo[b]pyran were dissolved in 34.9 g of ethanol and hydrogen gas was blown in the presence of 0.15 g of 5% palladium-carbon, as a catalyst, at room temperature for 3 hours under one atmospheric pressure while stirring. The reaction liquid was filtered under suction to remove the catalyst therefrom, and the solvent was distilled off to obtain 170 mg (yield: 94%) of 3,4-dihydro-2,2-dimethyl-3-hydroxy-4-(1-pyrrolidinyl)-6,7-diamino-2H-benzo[b]pyran as a dark red oil.

The whole amount of the diamino compound obtained in the previous step was dissolved in a mixture of 0.19 g of acetic acid and 0.34 g of water, and a solution prepared by dissolving 52 mg (0.75 mmol) of sodium nitrite in 0.22 g of water was added thereto all at a time at room temperature. After the generation of heat was recognized, the resulting mixture was heated on a water bath at 80° C. for 3 minutes. The compound was thereafter post-treated in the same manner as in Synthesis Example 53 to obtain 160 mg of the intended compound as an yellowish brown powder. The total yield through the two steps was 85%.

MS: 288(M$^+$, 3%), 270(M$^+$-H$_2$O, 3%), 216(M$^+$-72, 88%), 188(M$^+$-100, 100%), 70 (22%)

Synthesis Example 55

Synthesis of 7,8-dihydro-6,6-dimethyl-7-hydroxy-8-diethylamino-6H-pyrano[2,3-f]benzo-1,2,3-triazole

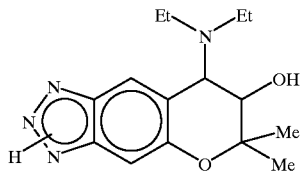

0.20 g (0.65 mmol) of 3,4-dihydro-2,2-dimethyl-3-hydroxy-4-diethylamino-6-amino-7-nitro-2H-benzo[b]pyran were dissolved in 34.9 g of ethanol and hydroge gas blown in in the presence of 0.15 g of 5% palladium-carbon, as a catalyst, for at room temperture for 2.5 hours under one atmospheric pressure while stirring. The reaction liquid was filtered under suction to remove the catalyst therefrom, and the solvent was distilledoff to obtain 0.15 g (yield: 83%) of 3,4-dihydro-2,2-dimethyl-3-hydroxy-4-diethylamino-6,7-diamino-2H-benzo[b]-pyran as a dark brown oil.

The whole amount of the diamino compound obtained in the previous step was dissolved in a mixture of 0.19 g of acetic acid and 0.34 g of water, and a solution prepared by dissolving 52 mg (0.75 mmol) of sodium nitrite in 0.22 g of water was added thereto all at a time at room temperature. After the generation of heat was recognized, the resulting mixture was heated on a water bath at 80° C. for 3 minutes. The mixture was thereafter post-treated in the same manner as in Synthesis Example 53 to obtain 70 mg of the intended compound as a pale brown powder. The total yield through the two steps was 37%.

MS(FAB): 291 [(M+H)$^+$]

Synthesis Example 56

Synthesis of 7,8-dihydro-6,6-dimethyl-7-hydroxy-8-(1-piperidinyl)-6H-pyrano[2,3-f]benzo-2,1,3-thiadiazole

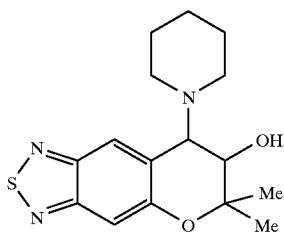

0.28 g (0.87 mmol) of 3,4-dihydro-2,2-dimethyl-3-hydroxy-4-(1-piperidinyl)-6-amino-7-nitro-2H-benzo[b]pyran was dissolved in 44.8 g of ethanol and hydrogen gas was blown in in the presence of 0.20 g of 5% palladium-carbon, as a catalyst, at room temperature for 3 hours under one atmospheric pressure while stirring. The reaction liquid was filtered under suction to remove the catalyst therefrom, and the solvent was removed by distillation to obtain 0.24 g (yield: 95%) of 3,4-dihydro-2,2-dimethyl-3-hydroxy-4-(1-piperidinyl)-6,7-diamino-2H-benzo[b]pyran as a dark red oil. 0.12 g (0.86 mmol) of thionylaniline and 4 g of benzenewere added thereto and heated under reflux for 2.5 hours. The solvent was distilled off under reduced pressure, and the residue was subjected to silica gel column chromatography (ethyl acetate-ethanol=1:3) to obtain 60 mg (yield: 23%) of the intended compound as an yellow solid.

MS: 84(85%), 247(100%), 319(M$^+$, 2%)

Synthesis Example 57

Synthesis of 7,8-dihydro-6,6-dimethyl-7-hydroxy-8-(1-pyrrolidinyl)-6H-pyrano[2,3-f]benzo-2,1,3-thiadiazole

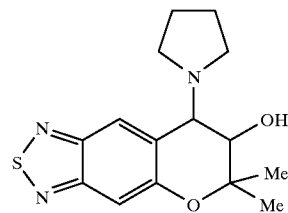

3,4-dihydro-2,2-dimethyl-3-hydroxy-4-(1-pyrrolidinyl)-6-amino-7-nitro-2H-benzo[b]pyran was processed in the same manner as in Synthesis Example 56 to obtain the intended compound as pale brown crystals. (yield: 25%)

Synthesis Example 58

Synthesis of 7,8-dihydro-6,6-dimethyl-7-hydroxy-8-diethylamino-6H-pyrano[2,3-f]benzo-2,1,3-thiadiazole

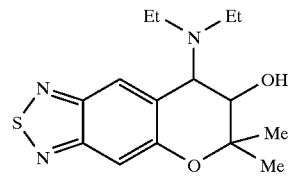

3,4-dihydro-2,2-dimethyl-3-hydroxy-4-diethylamino-6-amino-7-nitro-2H-benzo[b]pyran was processed in the same manner as in Synthesis Example 56 to obtain the intended compound as a brown oil. (yield: 17%)

Synthesis Example 59

Synthesis of (−)-7,8-dihydro-6,6-dimethyl-7-hydroxy-8-(1-pyrrolidinyl)-6H-pyrano[2,3-f]benzo-2,1,3-oxadiazole (optically-active (−) isomer of compound of Synthesis Example 4)

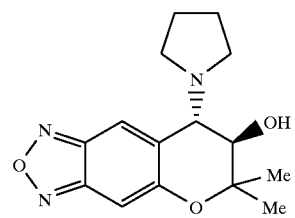

14.7 g (206.2 mmol) of pyrrolidine were added to 60 ml of an ethanol solution containing 15.0 g (68.7 mmol) of the compound of Reference Example 1 and heated under reflux for 2 hours. The solvent was distilled off under reduced pressure, 100 ml of water was added to the residue product, and was then extracted with chloroform (100 ml×1, 30 ml×2). After the chloroform solution was dried over anhydrous sodium sulfate, the solvent was distilled off under reduced pressure. The residue was subjected to silica gel column chromatography (benzene-ethyl acetate=5:1→4:1), and the crystals obtained were recrystallized from benzene : hexane (1:2) to obtain 13.8 g of the intended compound as yellow crystals. (yield: 69%)

240 ml of hydrochloric acid-methanol (10%) were added to 240 ml of a methanol solution containing 13 g (44.9 mmol) of the intended compound and stirred for 3 hours at room temperature. Then, the solvent was distilled off under reduced pressure. The residue was crystallized in 250 ml of 2-propanol to obtain 11.5 g of hydrochloride of the intended compound as colorless crystals. (yield: 78%)

m.p. >200° C. (decomposition).

Synthesis Example 60

Synthesis of (+)-7,8-dihydro-6,6-dimethyl-7-hydroxy-8-(1-pyrrolidinyl)-6H-pyrano[2,3-f]benzo-2,1,3-oxadiazole (optically-active (+) isomer of compound of Synthesis Example 4)

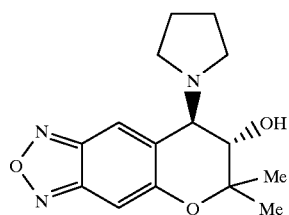

In the same manner as in Synthesis Example 59, 15.0 g (yield: 58%) of the intended compound were obtained as yellow crystals. Also in the same manner, 12.9 g (yield: 82%) of hydrochloride of the intended compound were obtained as colorless crystals.

m.p. >200° C. (decomposition).

Formulation Examples

Formulation Example 1

Formulation of Tablets:

| | |
|---|---|
| Compound (prepared in Synthesis Example 4) | 10 g |
| Lactose | 260 g |
| Crystal cellulose powder | 600 g |
| Corn Starch | 350 g |
| Hydroxypropyl cellulose | 100 g |
| CMC—Ca | 150 g |
| Magnesium stearate | 30 g |
| Total | 1500 g |

The above-mentioned components were mixed by a usual and then tabletted to produce 10,000 sugar-coated tablets, each containing one mg of the active ingredient.

Formulation Example 2

Formulation of Capsules:

| | |
|---|---|
| Compound (prepared in Synthesis Example 4) | 10 g |
| Lactose | 440 g |
| Crystal cellulose powder | 1000 g |
| Magnesium Stearate | 50 g |
| Total | 1500 g |

The above-mentioned components were mixed by a usual method and then packed in gelatin capsules to obtain 10,000 capsules, each containing one mg of the active ingredient.

Formulation Example 3

Formulation of Soft Capsules:

| | |
|---|---|
| Compound (prepared in Synthesis Example 4) | 10 g |
| PEG400 | 479 g |
| Saturated fatty acid triglyceride | 1500 g |
| Peppermint Oil | 1 g |
| Polysorbate 80 | 10 g |
| Total | 2000 g |

The above-mentioned components were mixed and packed in No. 3 soft gelatin capsules by a usual method to obtain 10,000 soft capsules, each containing one mg of the active ingredient.

Formulation Example 4

Formulation of Ointment:

| | |
|---|---|
| Compound (prepared in Synthesis Example 4) | 1.0 g |
| Liquid paraffin | 10.0 g |
| Cetanol | 20.0 g |
| Whilte vaseline | 68.4 g |
| Ethylparaben | 0.1 g |
| L-methol | 0.5 g |
| Total | 100.0 g |

The above-mentioned components were mixed by usual method to obtain 1% ointment.

Formulation Example 5

Formulation of Suppositories:

| | |
|---|---|
| Compound (prepared in Synthesis Example 4) | 1 g |
| Witepsol H15* | 478 g |
| Witepsol W35* | 520 g |
| Polysorbate 80 | 1 g |
| Total | 1000 g |

*Trade name for triglyceride compound

The above-mentioned components were melt-mixed by usual method and poured into suppository containers, followed by cooling for solidification to obtain 1,000 suppositories of 1 g, each containing one mg of the active ingredient.

Formulation Example 6

| Formulation of Injection: | |
|---|---|
| Compound (prepared in Synthesis Example 4) | 1 mg |
| Distilled water for injection | 5 ml |

The formulation is prepared by dissolving the compound in distilled water whenever it is required.

Pharmaceutical Test Examples
Effect on the contraction force of cardiac muscles
Test Method The heart was taken out from a m ale Hartley guinea pig, and the left atrium cordis was separated from it in a Krebs Henseleit liquid aerated with 95%-$O_2$/5%-$CO_2$. The specimen was overhung under tension of 0.5 g in an organ bath filled with anutrient liquid, which was kept at 31° C. To determine the force of cardiac muscles of the left atrium cordis, electric stimulation was transmularly imparted to the specimen via platinum bipolar electrodes and the tension generated by the contraction of force of cardiac muscles of the specimen was recorded. The conditions for the electric stimulation were as follows:

Voltage: two times the threshold potential to attain the contraction (V)

Time: 3 (m sec.)

Frequency: 1 (Hz)

After the specimen was equilibrated while exchanging the nutrient liquid, isoproterenol was accumulatively applied to the specimen to obtain the maximum contraction reaction of the specimen. After, the isoproterenol added was washed out, the specimen was again equilibrated for 60 minutes while exchanging the nutrient liquid. Afterwards, the test compounds mentioned below were applied to the specimen, while its action was observed.

The action caused by applying 100 $\mu$M and 300 $\mu$M of each compound are expressed by the rate of change (%), on the of the maximum contraction (100%) previously obtained when isoproterenol had been applied.

Results

The test results are shown in the following table, which verifies that the compounds of the present invention have a strong activity of enhancing the contraction of cardiac muscles and that the activity is dependent on the concentration of the compound applied.

Results of Test 1—effect on contraction force of cardiac muscles

| Test compound Synthesis | Rate of change (%) in constraction force of cardiac muscles | |
|---|---|---|
| Example No. | 100 $\mu$M | 300 $\mu$M |
| 1 | 24.7 | 52.7 |
| 2 | 44.2 | 84.0 |
| 3 | 55.7 | 135.0 |
| 36 | 67.5 | |

Effect on the rate of heart beats
Test Method

The heart was taken out from a male Hartley guinea pig, and the right atrium cordis was separated from it in a Krebs Henseleit liquid aerated with 95%-$O_2$/5%-$CO_2$. The specimen was overhung under tension of 1 g in an organ bath filled with a nutrient liquid, which was kept at 31° C.

After the specimen was equilibrated while exchanging the nutrient liquid, isoproterenol was accumulatively applied with the specimen to obtain the maximum reaction of the specimen. After, the isoproterenol applied was washed out, the specimen was again equilibrated for 60 minutes while exchanging the nutrient liquid. Afterwards, the test compounds mentioned below were applied to the specimen, while its reaction was observed.

The relative variation (%) in the rate of heart beats of the specimen due to the addition of the test compound (100 $\mu$M or 300 $\mu$M thereto was obtained, on the basis of the maximum reaction (100%) previously obtained when isoproterenol had been applied.

Results

The test results are shown in the following table, which verifies that the compounds of the present invention have an activity of reducing the rate of heart beats and that the activity is dependent on the concentration of the compound applied.

Results of Test 2—effect on the rate of heart beats

| Text compound (Synthesis | Variation (%) in the rate of hart beats | |
|---|---|---|
| Example No.) | 100 $\mu$M | 300 $\mu$M |
| 1 | −17.7 | −73.3 |
| 2 | −12.8 | −25.0 |
| 4 | −15.6 | −53.8 |

Effect on the cardiac function of anesthetized dogs
Test Method

Female and male mongrel dogs were anesthetized with sodium pentobarbital and kept under artificial respiration. A cannula was inserted into the abdominal aorta through the right crural artery, and the blood pressure of the animal was measured with a strain pressure amplifier via a pressure transducer. The rate of heart beats of the animal was measured on the basis of the moment heart beat wave, using the blood pressure wave as the trigger. A catheter pressure-transducer was inserted into the left ventricle from the left carotid artery, and the inner pressure in the left ventricle was measured via a strain pressure amplifier. The inner pressure in the left ventricle was differentiated via a differential unit to obtain the primary differentiated value of the inner pressure in the left ventricle (the value corresponds to the leading rate of the systolic pressure of the left ventricle, LV dp/dl$_{max}$). The test compounds mentioned below was dissolved in a mixed solvent of polyethylene glycol-400, ethanol and water (2:3:5) and introduced, with bolus dose, through a cannula inserted into the left cephalic vein of the animal. Prior to the test, it was recognized that the mixed solvent alone has no influence on the cardiac function and the blood pressure of the animal.

Results

The test results are shown in the following table, which verifies that the compounds of the present invention have a strong activity of enhancing the contraction of cardiac muscles and a strong activity of reducing the rate of heart beats without having any influence on the blood pressure.

Results of Test 3

(Effect of the compound of Synthesis Example 59 [(−)-isomer of the compound of Production Example 4)] intravenously administered to anesthetized dogs-variation (%) (as average of three tests) relative to the value obtained prior to addition of the compound)

|  | Amount Administered | Time (min) | | | | | |
| --- | --- | --- | --- | --- | --- | --- | --- |
| Tested Items | (mg/kg) | 0 | 1 | 3 | 5 | 10 | 20 |
| primary differentiated value of the inner pressure in the left ventricle | 1 | 0 | 14.3 | 8.0 | 3.1 | −0.8 | −2.4 |
|  | 3 | 0 | 18.9 | 13.5 | 9.1 | 4.3 | 1.4 |
| rate of heart beats | 1 | 0 | −5.7 | −5.8 | −5.2 | −4.0 | 4.1 |
|  | 3 | 0 | −10.6 | −11.0 | −10.4 | 7.0 | 5.0 |
| mean blood pressure | 1 | 0 | 1.0 | 0.1 | −0.1 | −0.4 | −2.3 |
|  | 3 | 0 | 2.6 | 2.0 | 2.5 | 2.3 | 3.2 |

We claim:

1. A method for treating cardiac insufficiency comprising administering an effective dose of, as an active ingredient, at least one compound of the following formula (I), their optical isomers, their stereoisomers and their pharmacologically acceptable salts when they may form salts:

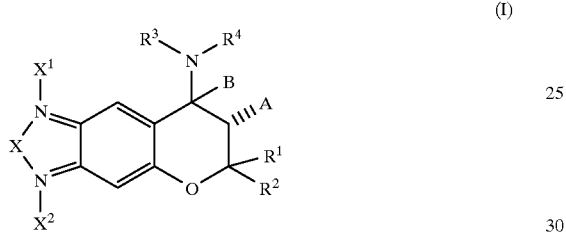

wherein $X^1$ and $X^2$ do not exist or represent an oxygen atom;

X represents an oxygen atom; a sulfur atom; a nitrogen atom, said nitrogen atom is unsubstituted or substituted by a hydrogen atom or a $C_1$–$C_4$ alkyl group; C(O); C(S); or C(N—CN);

A represents a hydrogen atom; a hydroxyl group; or OC(O)$R^5$ wherein $R^5$ represents a $C_1$–$C_4$ alkyl group; or may form a single bond together with B;

B represents a hydrogen atom, or may form a single bond together with A;

$R^1$ and $R^2$ are the same or different from each other and represent a hydrogen atom or a $C_1$–$C_4$ alkyl group, or $R^1$ and $R^2$ may together form a 1,4-butylene or 1,5-pentylene group which is unsubstituted or substituted by a $C_1$–$C_4$ alkyl group;

$R^3$ and $R^4$ are the same or different from each other and represent:

1) a hydrogen atom;
2) a $C_1$–$C_6$ alkyl group, said alkyl group is unsubstituted or substituted by one or more substituents selected from a halogen atom; a carboxyl group; a $C_2$–$C_5$ alkoxy carbonyl group; a hydroxyl group; a $C_1$–$C_4$ alkoxy group; CH(OR)$_2$ in which R represents a $C_1$–$C_4$ alkyl group; a phenyl group which is unsubstituted or substituted by one or more substituents selected from a halogen atom, a hydroxyl group and a $C_1$–$C_4$ alkoxy group; a formyl group; a cyano group and a nitro group;
3) a $C_2$–$C_6$ alkenyl group, said alkenyl group is unsubstituted or substituted by one or more substituents selected from a halogen atom; a carboxyl group; a $C_2$–$C_5$ alkoxycarbonyl group; a hydroxyl group; a $C_1$–$C_4$ alkoxy group; CH(OR)$_2$ in which R represents a $C_1$–$C_4$ alkyl group; a phenyl group which is unsubstituted or substituted by one or more substituents selected from a halogen atom, a hydroxyl group, and a $C_1$–$C_4$ alkoxy group, a formyl group; a cyano group and a nitro group;
4) a $C_2$–$C_6$ alkynyl group, said alkynyl group is unsubstituted or substituted by one or more substituents selected from a halogen atom; a carboxyl group; a $C_2$–$C_5$ alkoxycarbonyl group; a hydroxyl group; a $C_1$–$C_4$ alkoxy group; CH(OR)$_2$ in which R represents a $C_1$–$C_4$ alkyl group; a phenyl group which is unsubstituted or substituted by one or more substituents selected from a halogen atom, a hydroxyl group and a $C_1$–$C_4$ alkoxy group; a formyl group; a cyano group and a nitro group;
5) a $C_2$–$C_6$ cycloalkyl group, said cycloalkyl group is unsubstituted or substituted by one or more substituents selected from a halogen atom; a carboxyl group; a $C_2$–$C_5$ alkoxycarbonyl group; a hydroxyl group; a $C_1$–$C_4$ alkoxy group; CH(OR)$_2$ in which R represents a $C_1$–$C_4$ alkyl group; a phenyl group which is unsubstituted or substituted by one or more substituents selected from a halogen atom, a hydroxyl group and a $C_1$–$C_4$ alkoxy group; a formyl group; a cyano group and a nitro group;
6) a phenyl group which is unsubstituted or substituted by one or more substituents selected from a halogen atom, a hydroxyl group and a $C_1$–$C_4$ alkoxy group; or $R^3$ and $R^4$ may together form a 1,4-butylene or 1,5-pentylene group, said 1,4-butylene group and 1,5-pentylene group are unsubstituted or substituted by one or more substituents selected from a $C_1$–$C_4$ alkyl group; a phenyl group which is unsubstituted or substituted by one or more substituents selected from a halogen atom, a hydroxyl group and a $C_1$–$C_4$ alkoxy group; a halogen atom; $OR^{10}$ in which $R^{10}$ represents a hydrogen atom, a $C_1$–$C_4$ alkyl group; $COR^{11}$ wherein $R^{11}$ represents a $C_1$–$C_4$ alkyl group; a nitro group; $SO_3H$ or $PO_3H_2$; or $R^3$ and $R^4$ may together form $(CH_2)_m X^4 (CH_2)_1$, wherein m and 1 each represent 1, 2 or 3 while the sum of them is 3, 4 or 5; $X^4$ represents an oxygen atom; a sulfur atom; or $NR^{12}$ in which $R^{12}$ represents a hydrogen atom, a $C_1$–$C_4$ alkyl group, or a phenyl group which is unsubstituted or substituted by one or more substituents selected from a halogen atom, a hydroxyl group and a $C_1$–$C_4$ alkoxy group; or $R^3$ and $R^4$ may together form $(CH_2)_n ZC(=Y)$, wherein n represents 2, 3 or 4; and Y represents an oxygen atom; a sulfur atom, or $NR^7$ in which $R^7$ represents a hydrogen atom, a cyano group, a nitro group, a $C_1$–$C_4$ alkyl group, a $C_1$–$C_4$ alkoxy group or $CO_2R^8$ wherein $R^8$ represent a $C_1$–$C_4$ alkyl group; and Z represents an oxygen atom; a sulfur atom; or $NR^9$ in which $R^9$ represents a hydrogen atom, a $C_1$–$C_6$ alkyl group as defined above, a $C_2$–$C_6$ alkenyl group as defined above, a $C_2$–$C_6$ alkynyl group as defined above, a $C_3$–$C_6$ cycloalkyl group as defined above, or a phenyl group as defined above.

2. A method for treating cardiac insufficiency comprising administering an effective dose of, as the active ingredient, at least one compound of the following formula (II), their optical isomers, their stereoisomers and their pharmacologically acceptable salts when they may form salts:

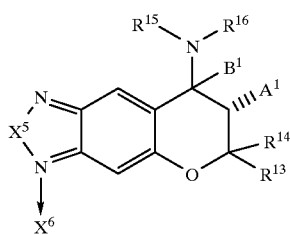

(II)

wherein $X^6$ does not exist or represents an oxygen atom;

$X^5$ represents an oxygen atom; a sulfur atom; or a nitrogen atom, said nitrogen atom is unsubstituted or substituted by a hydrogen atom or a $C_1$–$C_4$ alkyl group;

$A^1$ represents a hydrogen atom, a hydroxyl group, or $OC(O)R^{17}$ in which $R^{17}$ represents a $C_1$–$C_4$ alkyl group;

$B^1$ represents a hydrogen atom;

$R^{13}$ and $R^{14}$ are the same or different from each other and represent a hydrogen atom or a $C_1$–$C_4$ alkyl group;

$R^{15}$ and $R^{16}$ are the same or different from each other and represent:
1) a hydrogen atom;
2) a $C_1$–$C_6$ alkyl group, said alkyl group is unsubstituted or substituted by one or more substituents selected from a halogen atom; a carboxyl group; a $C_2$–$C_5$ alkoxycarbonyl group; a hydroxyl group; a $C_1$–$C_4$ alkoxy group; $CH(OR)_2$ in which R represents a $C_1$–$C_4$ alkyl group; a phenyl group which is unsubstituted or substituted by one or more substituents selected from a halogen atom, a hydroxyl group and a $C_1$–$C_4$ alkoxy group; a formyl group; a cyano group and a nitro group;
3) a $C_3$–$C_6$ cycloalkyl group, said cycloalkyl group is unsubstituted or substituted by one or more substituents selected from a halogen atom; a carboxyl group; a $C_2$–$C_5$ alkoxycarbonyl group; a hydroxyl group; a $C_1$–$C_4$ alkoxy group; $CH(OR)_2$ in which R represents a $C_1$–$C_4$ alkyl group; a phenyl group which is unsubstituted or substituted by one or more substituents selected from a halogen atom, a hydroxyl group and a $C_1$–$C_4$ alkoxy group; a formyl group; a cyano group and a nitro group;
4) a phenyl group which is unsubstituted or substituted by one or more substituents selected from a halogen atom, a hydroxyl group and a $C_1$–$C_4$ alkoxy group; or $R^{15}$ and $R^{16}$ may together form a 1,4-butylene or 1,5-pentylene group, said butylene and said pentylene are unsubstituted or substituted by one or more substituents selected from a $C_1$–$C_4$ alkyl group; a phenyl group which is unsubstituted or substituted by one or more substituents selected from a halogen atom, a hydroxyl group and a $C_1$–$C_4$ alkoxy group; a halogen atom, $OR^{21}$ in which $R^{21}$ represents a hydrogen atom, a $C_1$–$C_4$ alkyl group, $COR^{22}$ wherein $R^{22}$ represents a $C_1$–$C_4$ alkyl group; a nitro group; $SO_3H$ or $PO_3H_2$; or $R^{15}$ and $R^{16}$ may together form $(CH_2)_oX^7(CH_2)_p$ wherein o and p each is an integer of 1, 2 or 3 while the sum of them is 3, 4 or 5;

$X^7$ represents an oxygen atom; a sulfur atom; or $NR^{23}$, wherein $R^{23}$ represents a hydrogen atom, a $C_1$–$C_4$ alkyl group, or a phenyl group which is unsubstituted or substituted by one or more substituents selected from a halogen atom, a hydroxyl group and a $C_1$–$C_4$ alkoxy group; or $R^{15}$ and $R^{16}$ may together form $(CH_2)_QZ^1C(=Y^1)$, wherein Q represents an integer of 2, 3 or 4; and $Y^1$ represents an oxygen atom; a sulfur atom; or $NR^{19}$, wherein $R^{19}$ represents a hydrogen atom, a cyano group, a nitro group, a $C_1$–$C_4$ alkyl group or a $C_1$–$C_4$ alkoxy group; and $Z^1$ represents an oxygen atom; a sulfur atom; or $NR^{20}$, wherein $R^{20}$ represents a hydrogen atom, a $C_1$–$C_6$ alkyl group as defined above; a $C_3$–$C_6$ cycloalkyl group as defined above; or a phenyl group as defined above.

3. The method for treating cardiac insufficiency as claimed in claim 2, wherein $R^{15}$ in formula (II) represents a hydrogen atom; and $R^{16}$ represents $C(=Y^2)NHR^{24}$, wherein $Y^2$ represents an oxygen atom, a sulfur atom or N—CN; and $R^{24}$ represents a phenyl group, a benzyl group or a $C_1$–$C_8$ alkyl group which may be branched.

4. The method for treating cardiac insufficiency as claimed in claim 2, wherein $R^{15}$ and $R^{16}$ in formula (II) together form $(CH_{2k}NHC(=Y^3)$, wherein k is an integer of 2, 3 or 4; and $Y^3$ represents an oxygen atom, a sulfur atom or N—CN.

5. The method for treating cardiac insufficiency as claimed in claim 2, in which $R^{15}$ and $R^{16}$ in formula (II) simultaneously represent $C_1$–$C_6$ alkyl groups.

6. The method for treating cardiac insufficiency as claimed in claim 2, in which $R^{15}$ and $R^{16}$ in formula (II) together form $(CH_2)_4$ or $(CH_2)_5$.

* * * * *